United States Patent
Choung et al.

(10) Patent No.: US 11,202,621 B2
(45) Date of Patent: Dec. 21, 2021

(54) ADJUSTABLE TARGETING SET FOR MRI GUIDED BIOPSY PROCEDURE

(71) Applicant: Devicor Medical Products, Inc., Cincinnati, OH (US)

(72) Inventors: Rachel Yoon Choung, Studio City, CA (US); John Kevin Bruce, Burlington, KY (US)

(73) Assignee: Devicor Medical Products, Cincinnati, OH (US)

( * ) Notice: Subject to any disclaimer, the term of this patent is extended or adjusted under 35 U.S.C. 154(b) by 345 days.

(21) Appl. No.: 16/197,463

(22) Filed: Nov. 21, 2018

(65) Prior Publication Data
US 2019/0150900 A1    May 23, 2019

Related U.S. Application Data

(60) Provisional application No. 62/589,785, filed on Nov. 22, 2017.

(51) Int. Cl.
| | |
|---|---|
| *A61B 5/00* | (2006.01) |
| *A61B 10/02* | (2006.01) |
| *A61B 17/34* | (2006.01) |
| *A61B 90/00* | (2016.01) |
| *A61B 90/11* | (2016.01) |

(52) U.S. Cl.
CPC ...... *A61B 10/0275* (2013.01); *A61B 10/0283* (2013.01); *A61B 17/3403* (2013.01); *A61B 17/3421* (2013.01); *A61B 90/11* (2016.02); *A61B 90/37* (2016.02); *A61B 2010/0208* (2013.01); *A61B 2017/3405* (2013.01); *A61B 2017/3411* (2013.01);

(Continued)

(58) Field of Classification Search
CPC . A61B 10/0275; A61B 90/11; A61B 17/3403; A61B 10/0283; A61B 90/37; A61B 17/3421; A61B 2090/0807; A61B 2090/034; A61B 2090/062; A61B 2017/3405; A61B 2010/0208; A61B 2017/3411; A61B 2090/374
USPC ................................... 600/562–565
See application file for complete search history.

(56) References Cited

U.S. PATENT DOCUMENTS 5,290,304 A * 3/1994 Storace ............. A61B 17/3496
30/366
5,320,610 A * 6/1994 Yoon ................. A61B 17/3496
604/158

(Continued)

OTHER PUBLICATIONS

International Search Report and Written Opinion dated Apr. 16, 2019 for International Application No. PCT/US2018/062173, 15 pages.

(Continued)

*Primary Examiner* — May A Abouelela
(74) *Attorney, Agent, or Firm* — Frost Brown Todd LLC

(57) ABSTRACT

A targeting set for use with positioning a biopsy device within a patient. The targeting set includes an obturator and an actuator. The actuator includes a housing and a lock array. The lock array extends inwardly within a hollow interior defined by the housing. The obturator is configured for insertion into the housing of the actuator such that at least a portion of the obturator engages the lock array. The lock array is configured to selectively lock the obturator in a plurality of axial positions relative to the housing.

13 Claims, 16 Drawing Sheets

(52) U.S. Cl.
CPC ... *A61B 2090/034* (2016.02); *A61B 2090/062* (2016.02); *A61B 2090/0807* (2016.02); *A61B 2090/374* (2016.02)

(56) References Cited

U.S. PATENT DOCUMENTS

| | | | |
|---|---|---|---|
| 5,336,176 A | 8/1994 | Yoon | |
| 5,388,589 A * | 2/1995 | Davis | A61B 10/0275 600/562 |
| 5,423,824 A * | 6/1995 | Akerfeldt | A61B 10/025 600/567 |
| 5,526,822 A | 6/1996 | Burbank et al. | |
| 5,645,076 A | 7/1997 | Yoon | |
| 5,868,785 A * | 2/1999 | Tai | A61B 17/29 606/207 |
| 5,928,164 A | 7/1999 | Burbank et al. | |
| 6,017,316 A | 1/2000 | Ritchart et al. | |
| 6,033,411 A * | 3/2000 | Preissman | A61B 17/3472 604/165.01 |
| 6,086,544 A | 4/2000 | Hibner et al. | |
| 6,162,187 A | 12/2000 | Buzzard et al. | |
| 6,358,217 B1 * | 3/2002 | Bourassa | A61B 10/0275 600/567 |
| 6,432,065 B1 | 8/2002 | Burdorff et al. | |
| 6,595,979 B1 * | 7/2003 | Epstein | A61M 5/1456 604/506 |
| 6,626,849 B2 | 9/2003 | Huitema et al. | |
| 6,685,724 B1 * | 2/2004 | Haluck | A61B 17/29 606/207 |
| 6,752,768 B2 | 6/2004 | Burdorff et al. | |
| 7,442,171 B2 | 10/2008 | Stephens et al. | |
| 7,507,210 B2 * | 3/2009 | Hibner | A61B 10/0266 600/567 |
| 7,648,466 B2 | 1/2010 | Stephens et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,938,786 B2 | 5/2011 | Ritchie et al. | |
| 8,083,687 B2 | 12/2011 | Parihar | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,277,394 B2 | 10/2012 | Hibner | |
| 8,328,732 B2 | 12/2012 | Parihar et al. | |
| 8,454,531 B2 | 6/2013 | Speeg et al. | |
| 8,622,924 B2 | 1/2014 | Speeg et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,028,401 B1 * | 5/2015 | Bacich | A61F 6/22 600/204 |
| 9,078,640 B1 * | 7/2015 | An | A61B 10/0283 |
| 9,095,326 B2 | 8/2015 | Ritchie et al. | |
| 9,326,755 B2 | 5/2016 | Fiebig et al. | |
| 9,345,457 B2 | 5/2016 | Speeg et al. | |
| 9,931,104 B2 | 4/2018 | Rhad et al. | |
| 2006/0074345 A1 | 4/2006 | Hibner | |
| 2007/0149893 A1 * | 6/2007 | Heske | A61B 10/0275 600/566 |
| 2007/0167868 A1 * | 7/2007 | Sauer | A61B 10/0233 600/564 |
| 2007/0255168 A1 | 11/2007 | Hibner et al. | |
| 2008/0228103 A1 | 9/2008 | Ritchie et al. | |
| 2009/0131821 A1 | 5/2009 | Speeg et al. | |
| 2010/0034605 A1 * | 2/2010 | Huckins | A61B 17/1739 408/1 R |
| 2010/0152610 A1 | 6/2010 | Parihar et al. | |
| 2010/0160816 A1 * | 6/2010 | Parihar | A61B 10/0096 600/564 |
| 2010/0160819 A1 | 6/2010 | Parihar et al. | |
| 2010/0160824 A1 | 6/2010 | Parihar et al. | |
| 2010/0286486 A1 * | 11/2010 | Parker | A61B 90/35 600/235 |
| 2012/0065542 A1 | 3/2012 | Hibner et al. | |
| 2012/0157880 A1 * | 6/2012 | Haseby | A61B 10/0233 600/567 |
| 2012/0172752 A1 * | 7/2012 | Ranpura | A61B 10/0275 600/567 |
| 2012/0191006 A1 * | 7/2012 | Ostrovsky | A61B 17/00 600/562 |
| 2013/0144188 A1 | 6/2013 | Fiebig et al. | |
| 2013/0324882 A1 | 12/2013 | Mescher | |
| 2014/0039343 A1 | 2/2014 | Mescher et al. | |
| 2014/0088432 A1 * | 3/2014 | Ryan | A61B 8/12 600/471 |
| 2014/0228705 A1 * | 8/2014 | Linderman | A61B 10/0283 600/566 |
| 2015/0012008 A1 * | 1/2015 | McWeeney | A61B 17/3423 606/108 |
| 2015/0025414 A1 | 1/2015 | Rhad et al. | |
| 2015/0065913 A1 | 3/2015 | Keller et al. | |
| 2016/0100858 A1 | 4/2016 | Flom et al. | |
| 2018/0028193 A1 * | 2/2018 | Mathis | A61B 17/12145 |
| 2018/0333147 A1 * | 11/2018 | Snow | A61B 10/0275 |
| 2020/0077991 A1 * | 3/2020 | Gordon | A61B 10/04 |

OTHER PUBLICATIONS

U.S. Appl. No. 62/157,586, filed May 6, 2015, entitled "MRI Guided Biopsy Targeting Assembly with Obturator Overshoot Feature."

* cited by examiner

ADJUSTABLE TARGETING SET FOR MRI GUIDED BIOPSY PROCEDURE

PRIORITY

This application claims priority to U.S. Provisional Patent App. No. 62/589,785 entitled "Adjustable Targeting Set for MRI Guided Biopsy Procedure," filed Nov. 22, 2017, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by an operator using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 7,442,171, entitled "Remote Thumbwheel for a Surgical Biopsy Device," issued Oct. 8, 2008; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 21, 2012; U.S. Pat. No. 8,206,316, entitled "Tetherless Biopsy Device with Reusable Portion," issued Jun. 26, 2012; U.S. Pat. No. 8,764,680, entitled "Handheld Biopsy Device with Needle Firing," issued Jul. 1, 2014; and U.S. Pat. No. 9,345,457, entitled "Presentation of Biopsy Sample by Biopsy Device," issued May 24, 2016. The disclosure of each of the above-cited U.S. patents is incorporated by reference herein.

One merely illustrative localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The depth of insertion for the obturator and targeting cannula can generally be set using a z-stop that is selectively fastenable to the exterior of the targeting cannula. The obturator may then be removed, and the needle of a biopsy device may then be inserted through the targeting cannula/sleeve to reach the targeted lesion.

Although the configuration described above generally has substantial utility in the context of MRI biopsy procedures, some challenges may still exist. For instance, in some circumstances it may be difficult to grip the obturator and/or targeting cannula. In other circumstances it may be difficult to manipulate the z-stop, particularly in the tight confines of the localization mechanism. In view of this, in some circumstances it may be desirable to provide certain modifications to the configuration described above to promote enhanced ease of use. While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
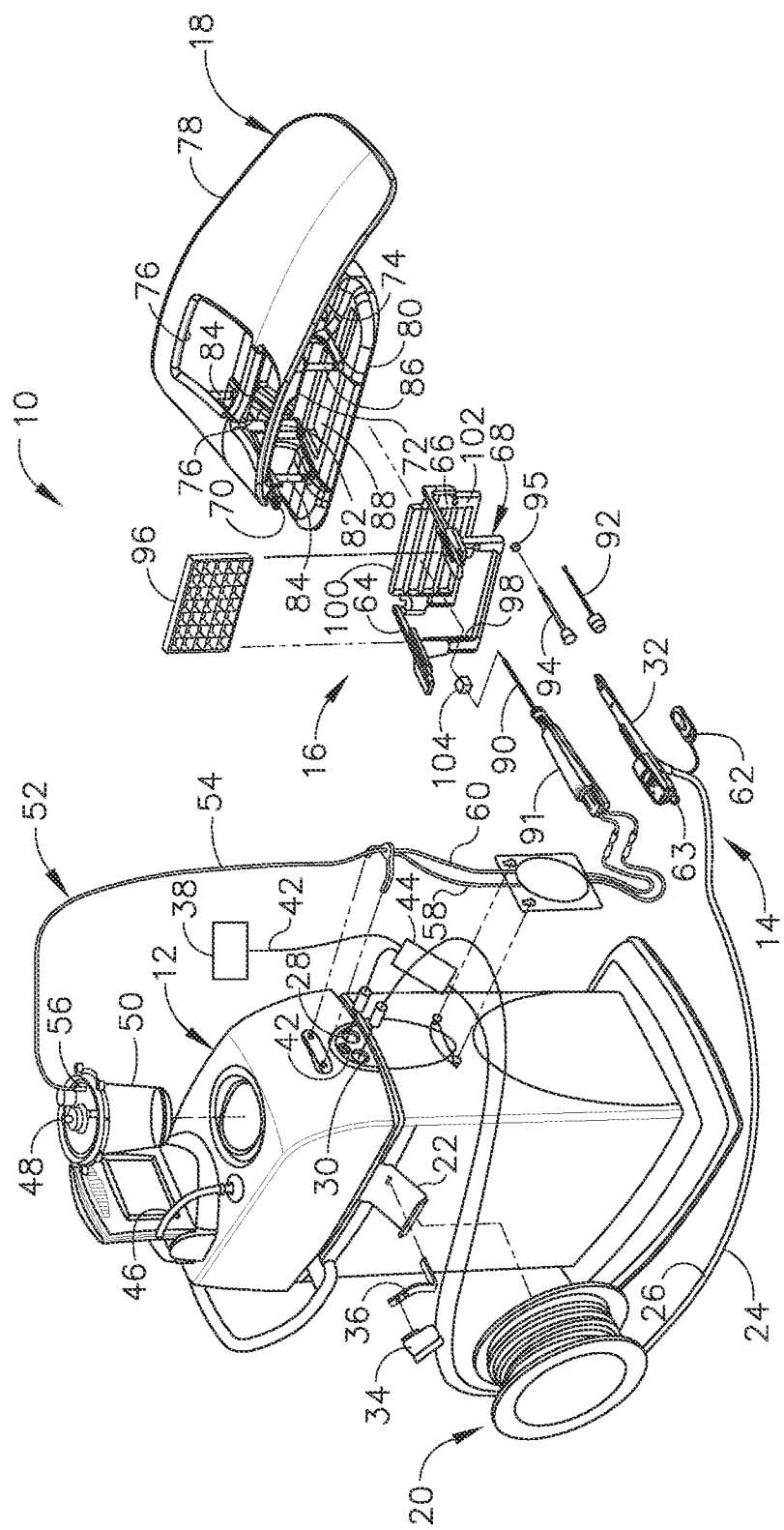
FIG. 1 depicts a perspective view of a biopsy system including a control module remotely coupled to a biopsy device, and including a localization fixture with a lateral grid plate used in conjunction with a rotatable cube to position an obturator or a probe of the biopsy device to a desired insertion depth as set by a ring stop.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. OVERVIEW OF EXEMPLARY MRI BIOPSY CONTROL MODULE

Figure 2:
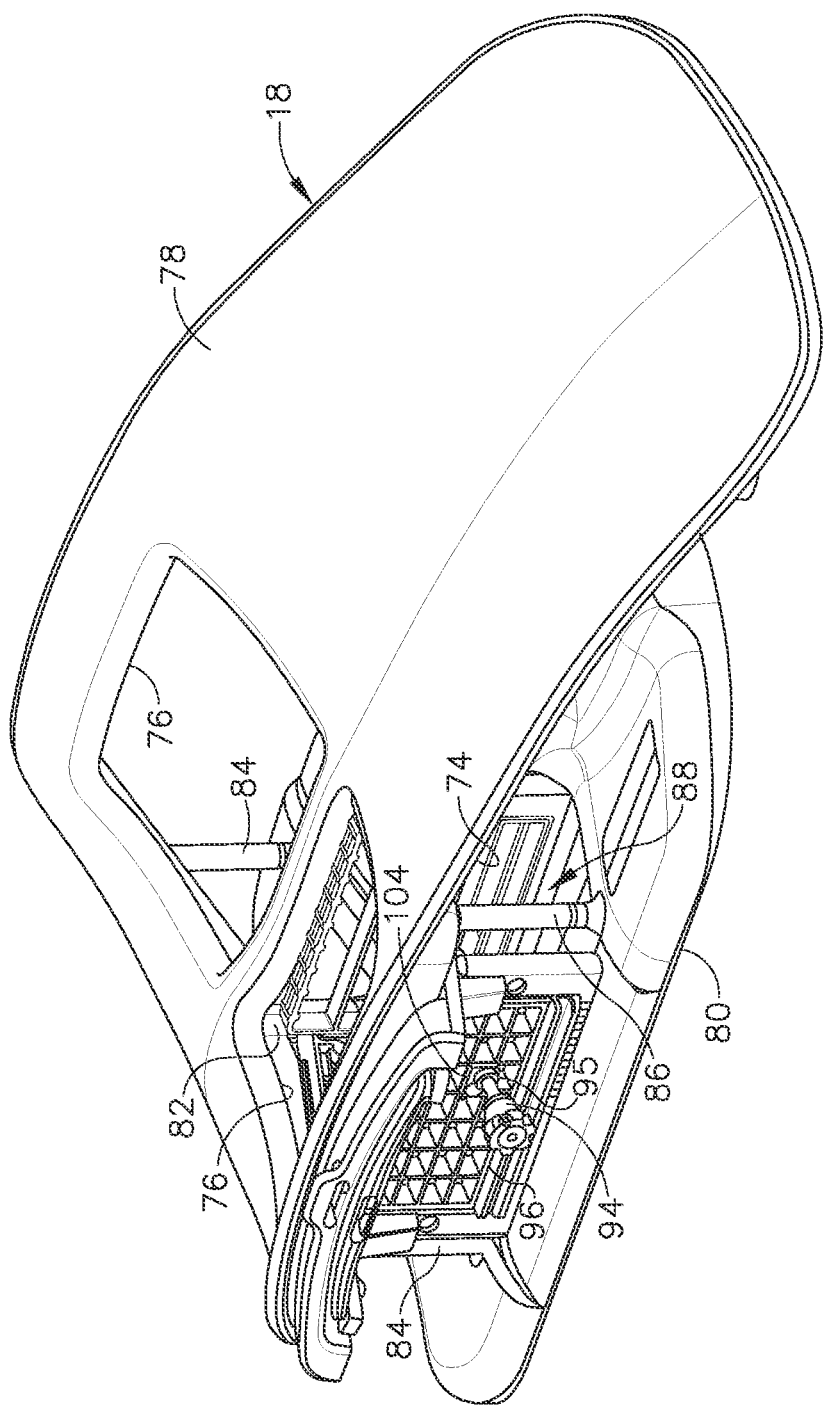
FIG. 2 depicts a perspective view of a breast coil receiving the localization fixture of FIG. 1.
Figure 3:
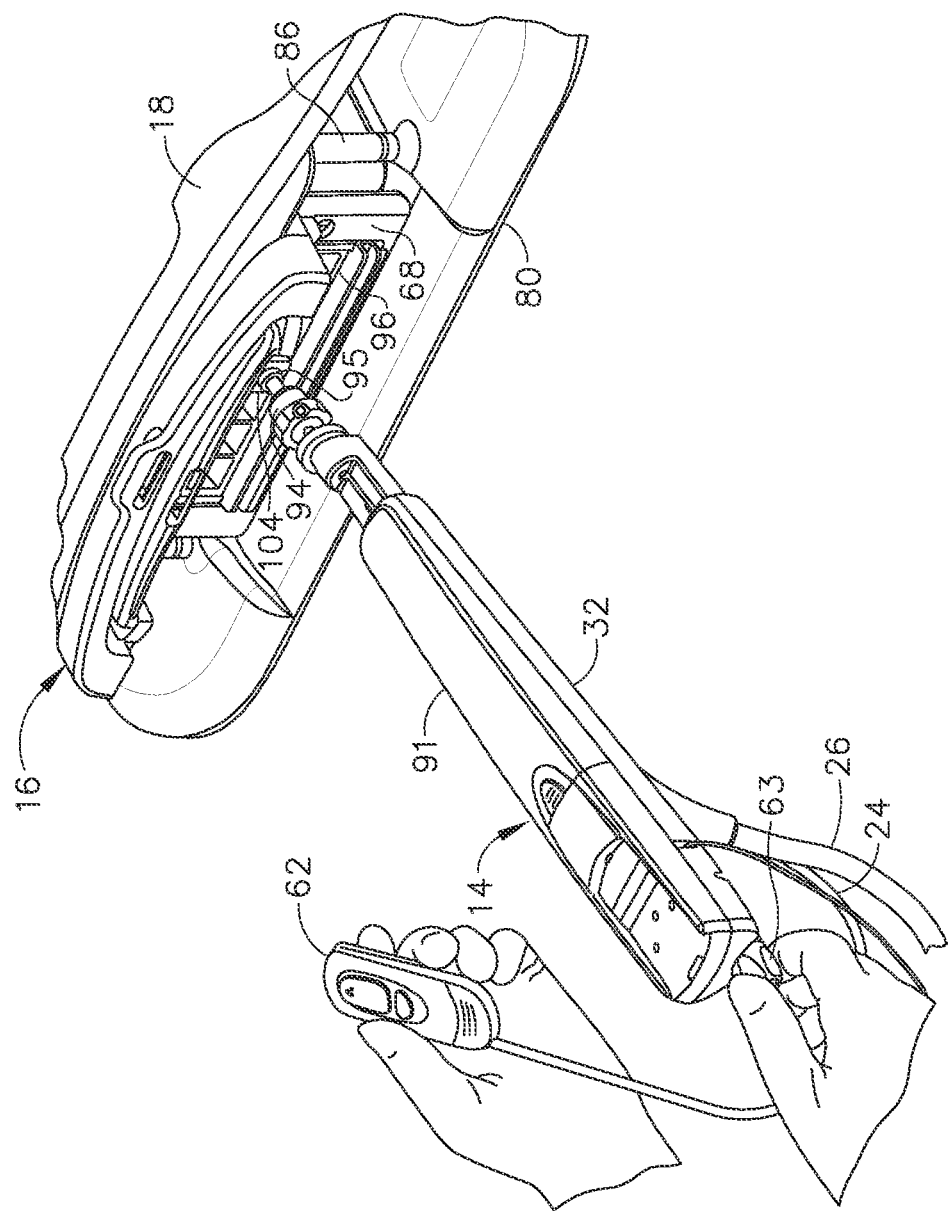
FIG. 3 depicts a perspective view of the biopsy device inserted through the rotatable cube within the cube plate of the localization fixture attached to the breast coil of FIG. 2.

In FIGS. 1-3, an MRI compatible biopsy system (10) has control module (12) that may be placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality may be incorporated into control module (12) to assist in taking tissue samples. Control module (12) controls and powers biopsy device (14) that is used with localization assembly (15). Biopsy device (14) is positioned and guided by localization fixture (16) attached to breast coil (18) that may be placed upon a gantry (not shown) of a MRI or other imaging machine.

In the present example, control module (12) is mechanically, electrically, and pneumatically coupled to biopsy device (14) so that components may be segregated that need to be spaced away from the strong magnetic field and the sensitive RF receiving components of a MRI machine. Cable management spool (20) is placed upon cable management attachment saddle (22) that projects from a side of control module (12). Wound upon cable management spool (20) is paired electrical cable (24) and mechanical cable (26) for communicating control signals and cutter rotation/advancement motions respectively. In particular, electrical and mechanical cables (24, 26) each have one end connected to respective electrical and mechanical ports (28, 30) in control module (12) and another end connected to holster portion (32) of biopsy device (14). Docking cup (34), which may hold holster portion (32) when not in use, is hooked to control module (12) by docking station mounting bracket (36). It should be understood that such components described above as being associated with control module (12) are merely optional.

Interface lock box (38) mounted to a wall provides tether (40) to lockout port (42) on control module (12). Tether (40) is uniquely terminated and of short length to preclude inadvertent positioning of control module (12) too close to a MRI machine or other machine. In-line enclosure (44) may register tether (40), electrical cable (24) and mechanical cable (26) to their respective ports (42, 28, 30) on control module (12).

Vacuum assist is provided by first vacuum line (46) that connects between control module (12) and outlet port (48) of vacuum canister (50) that catches liquid and solid debris. Tubing kit (52) completes the pneumatic communication between control module (12) and biopsy device (14). In particular, second vacuum line (54) is connected to inlet port (56) of vacuum canister (50). Second vacuum line (54) divides into two vacuum lines (58, 60) that are attached to biopsy device (14). With biopsy device (14) installed in holster portion (32), control module (12) performs a functional check. Saline may be manually injected into biopsy device (14) or otherwise introduced to biopsy device (14), such as to serve as a lubricant and to assist in achieving a vacuum seal and/or for other purposes. Control module (12) actuates a cutter mechanism (not shown) in biopsy device (14), monitoring full travel of a cutter in biopsy device (14) in the present example. Binding in mechanical cable (26) or within biopsy device (14) may optionally monitored with reference to motor force exerted to turn mechanical cable (26) and/or an amount of twist in mechanical cable (26) sensed in comparing rotary speed or position at each end of mechanical cable (26).

Remote keypad (62), which is detachable from holster portion (32), communicates via electrical cable (24) to control panel (12) to enhance clinician control of biopsy device (14) in the present example, especially when controls that would otherwise be on biopsy device (14) itself are not readily accessible after insertion into localization fixture (16) and/or placement of control module (12) is inconveniently remote (e.g., 30 feet away). However, as with other components described herein, remote keypad (62) is merely optional, and may be modified, substituted, supplemented, or omitted as desired. In the present example, aft end thumbwheel (63) on holster portion (32) is also readily accessible after insertion to rotate the side from which a tissue sample is to be taken.

Of course, the above-described control module (12) is merely one example. Any other suitable type of control module (12) and associated components may be used. By way of example only, control module (12) may instead be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, control module (12) may instead be configured and operable in accordance with the teachings of U.S. Pat. No. 8,328,732, entitled "Control Module Interface for MRI Biopsy Device," issued Dec. 11, 2012, the disclosure of which is incorporated by reference herein. Alternatively, control module (12) may have any other suitable components, features, configurations, functionalities, operability, etc. Other suitable variations of control module (12) and associated components will be apparent to those of ordinary skill in the art in view of the teachings herein.

II. EXEMPLARY LOCALIZATION ASSEMBLY

Left and right parallel upper guides (64, 66) of localization framework (68) are laterally adjustably received respectively within left and right parallel upper tracks (70, 72) attached to under side (74) and to each side of a selected breast aperture (76) formed in patient support platform (78) of breast coil (18). Base (80) of breast coil (18) is connected by centerline pillars (82) that are attached to patient support platform (78) between breast apertures (76). Also, a pair of outer vertical support pillars (84, 86) on each side spaced about a respective breast aperture (76) respectively define lateral recess (88) within which localization fixture (16) resides.

It should be appreciated that the patient's breasts hang pendulously respectively into breast apertures (76) within lateral recesses (88) in the present example. For convenience, herein a convention is used for locating a suspicious lesion by Cartesian coordinates within breast tissue referenced to localization fixture (16) and to thereafter selectively position an instrument, such as needle (90) of probe (91) that is engaged to holster portion (32) to form biopsy device (14). Of course, any other type of coordinate system or targeting techniques may be used. To enhance hands-off use of biopsy system (10), especially for repeated re-imaging within the narrow confines of a closed bore MRI machine, biopsy system (10) may also guide obturator (92) encompassed by cannula (94). Depth of insertion is controlled by depth stop device (95) longitudinally positioned on either needle (90) or cannula (94). Alternatively, depth of insertion may be controlled in any other suitable fashion.

This guidance is specifically provided by a lateral fence in the present example, depicted as grid plate (96), which is received within laterally adjustable outer three-sided plate bracket (98) attached below left and right parallel upper guides (64, 66). Similarly, a medial fence with respect to a medial plane of the chest of the patient, depicted as medial plate (100), is received within inner three-sided plate bracket (102) attached below left and right parallel upper guides (64, 66) close to centerline pillars (82) when installed in breast coil (18). To further refine the insertion point of the instrument (e.g., needle (90) of probe (91), obturator/cannula (92, 94), etc.), guide cube (104) may be inserted into grid plate (96).

In the present example, the selected breast is compressed along an inner (medial) side by medial plate (100) and on an outer (lateral) side of the breast by grid plate (96), the latter defining an X-Y plane. The X-axis is vertical (sagittal) with respect to a standing patient and corresponds to a left-to-right axis as viewed by a clinician facing the externally exposed portion of localization fixture (16). Perpendicular to this X-Y plane extending toward the medial side of the breast is the Z-axis, which typically corresponds to the orientation and depth of insertion of needle (90) or obturator/cannula (92, 94) of biopsy device (14). For clarity, the term Z-axis may be used interchangeably with "axis of penetration", although the latter may or may not be orthogonal to the spatial coordinates used to locate an insertion point on the patient. Versions of localization fixture (16) described herein allow a non-orthogonal axis of penetration to the X-Y axis to a lesion at a convenient or clinically beneficial angle.

It should be understood that the above-described localization assembly (15) is merely one example. Any other suitable type of localization assembly (15) may be used, including but not limited to localization assemblies (15) that use a breast coil (18) and/or localization fixture (16) different from those described above. Other suitable components, features, configurations, functionalities, operability, etc. for a localization assembly (15) will be apparent to those of ordinary skill in the art in view of the teachings herein.

III. EXEMPLARY BIOPSY DEVICE

As shown in FIG. 1, one version of biopsy device (14) may comprise holster portion (32) and probe (91). Exemplary holster portion (32) was discussed previously in the above section addressing control module (12). The following paragraphs will discuss probe (91) and associated components and devices in further detail.

Figure 7:
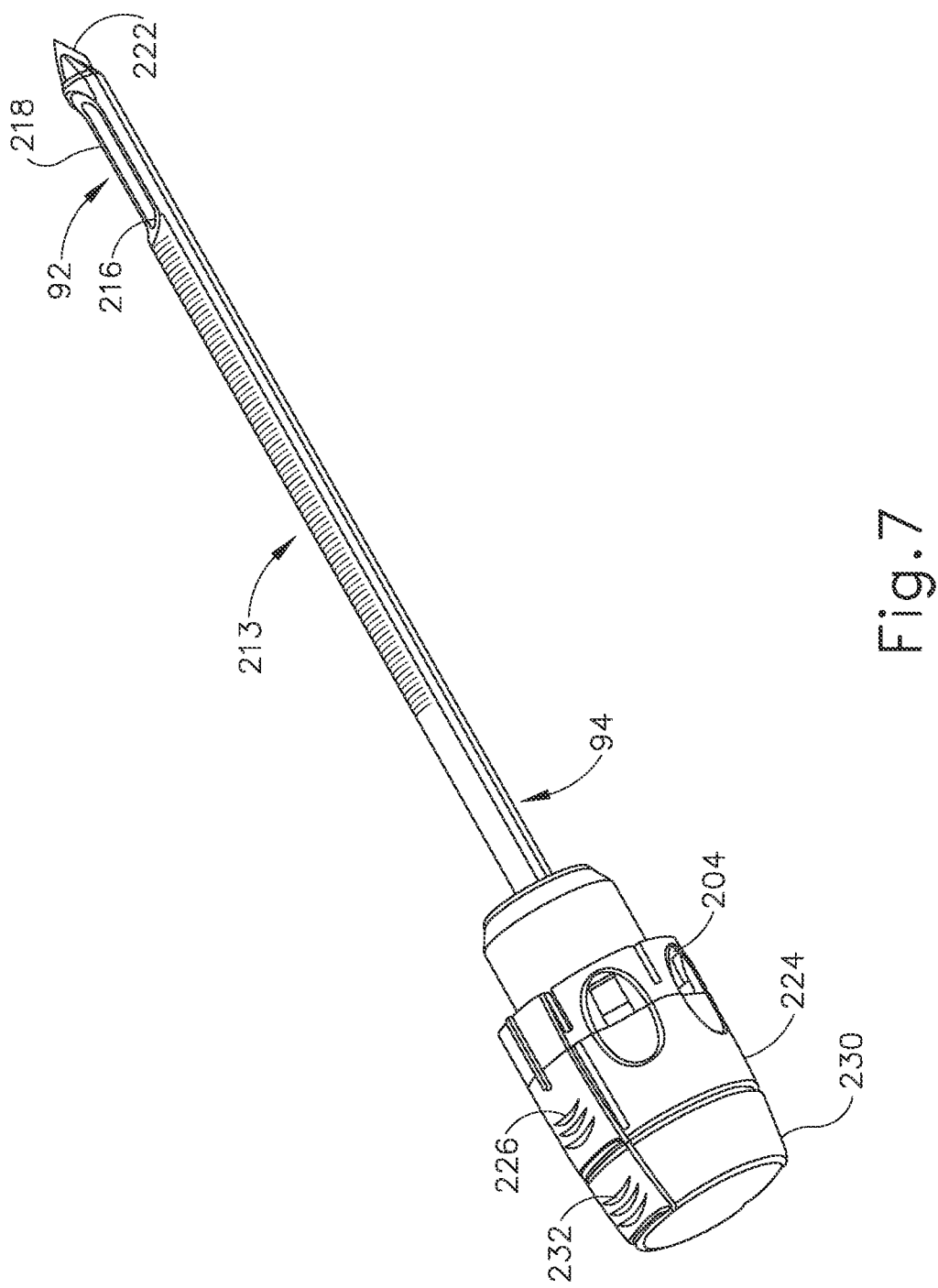
FIG. 7 depicts a perspective view of an obturator and cannula of the biopsy system of FIG. 1.
Figure 8:
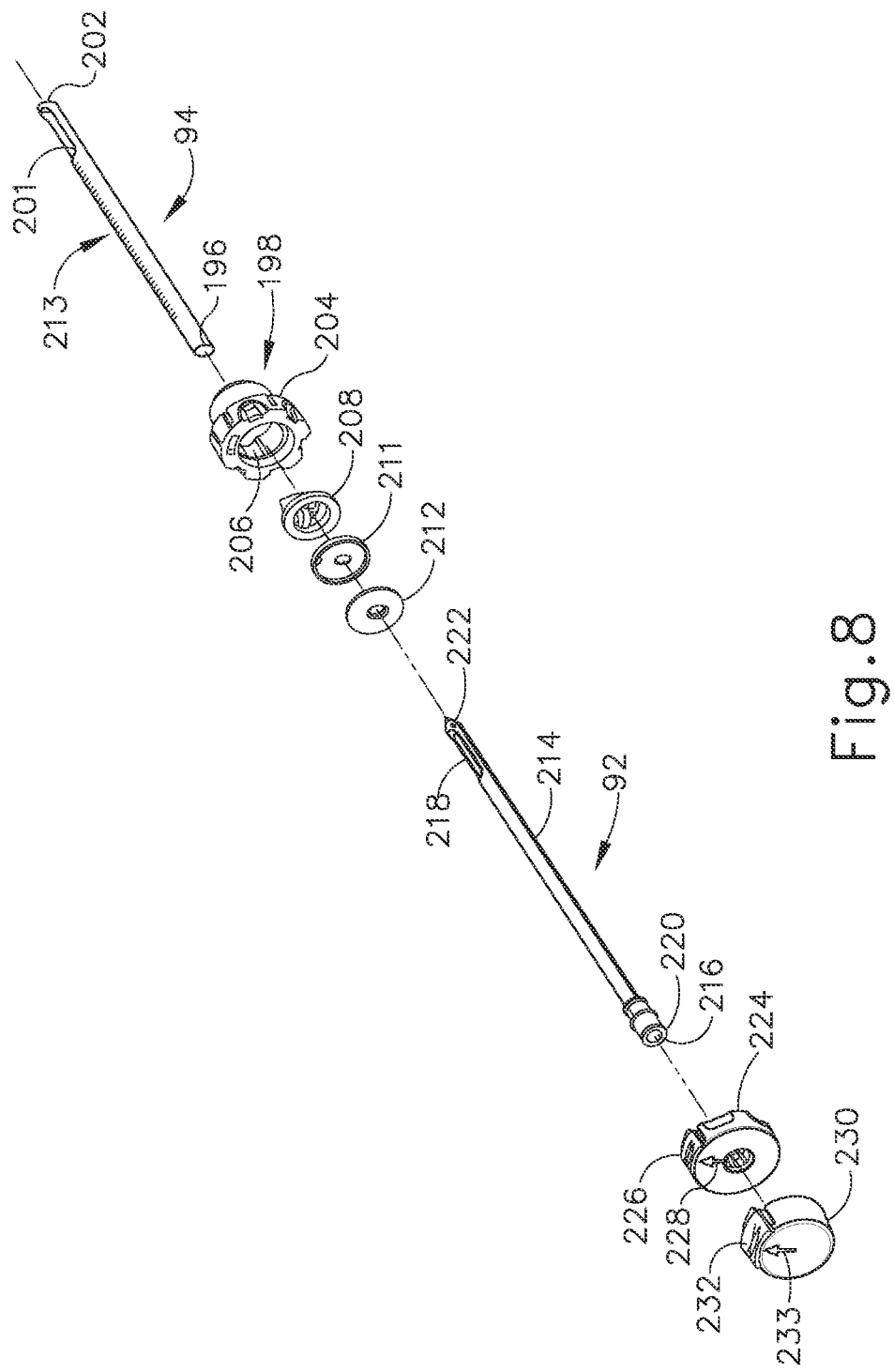
FIG. 8 depicts a perspective exploded view of the obturator and cannula of FIG. 7.
Figure 9:
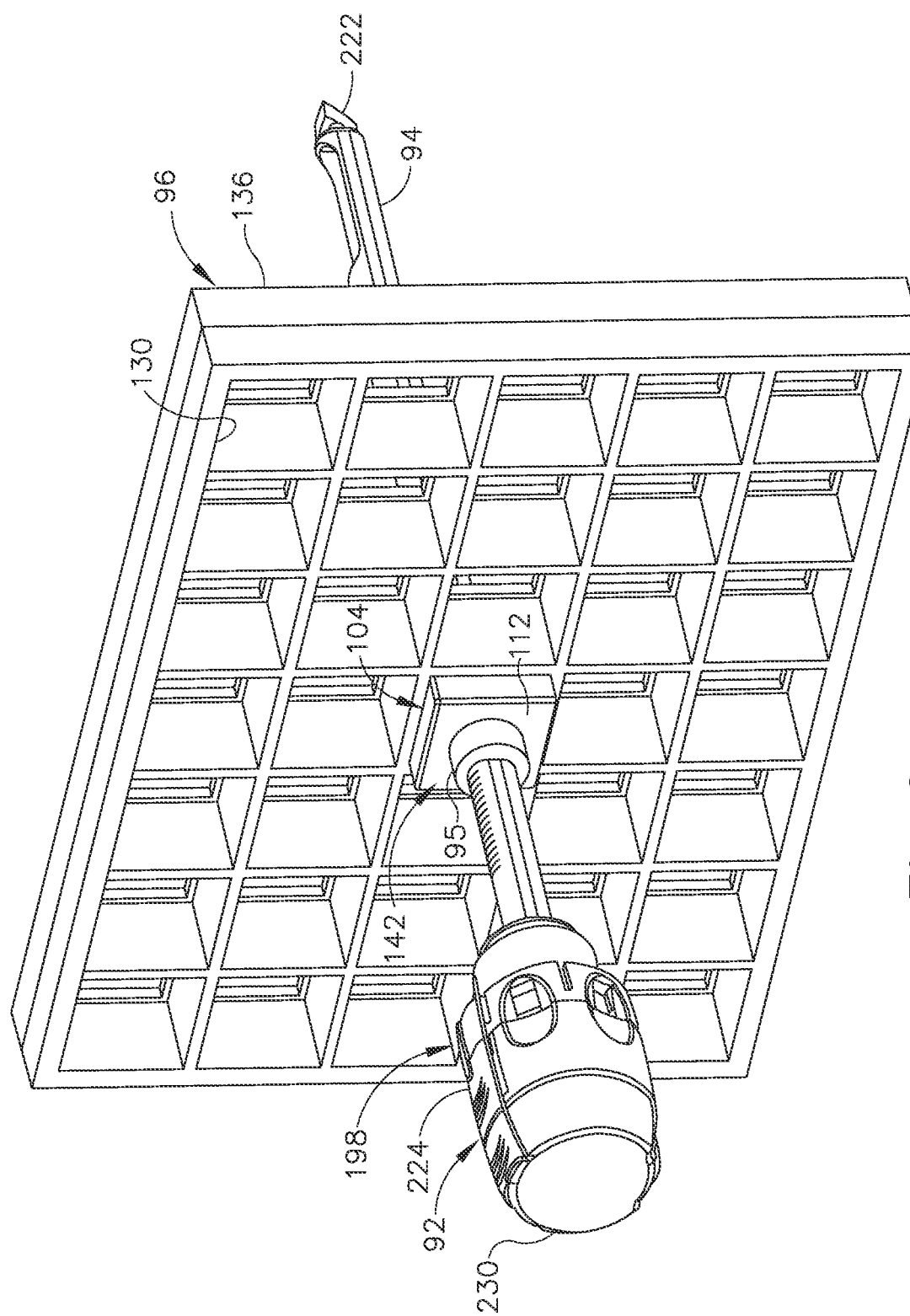
FIG. 9 depicts a perspective view of the obturator and cannula of FIG. 7 with a depth stop device of FIG. 1 inserted through the guide cube and grid plate of FIG. 6.

In the present example, a targeting set (89) comprising cannula (94) and a stylet or obturator (92) is associated with probe (91). In particular, and as shown in FIGS. 7, 8, and 9, obturator (92) is slid into cannula (94) and the combination is guided through guide cube (104) to the biopsy site within the breast tissue. As shown in FIG. 3, obturator (92) is then withdrawn from cannula (94), then needle (90) of probe (91) is inserted in cannula (94), and then biopsy device (14) is operated to acquire one or more tissue samples from the breast via needle (90).

As best seen in FIG. 8, cannula (94) of the present example is proximally attached to cylindrical hub (198) and cannula (94) includes lumen (196) and lateral aperture (201) proximate to open distal end (202). Cylindrical hub (198) has exteriorly presented thumbwheel (204) for rotating lateral aperture (201). Cylindrical hub (198) has interior recess (206) that encompasses duckbill seal (208), wiper seal (211) and seal retainer (212) to provide a fluid seal when lumen (196) is empty and for sealing to inserted obturator (92). Longitudinally spaced measurement indicia (213) along an outer surface of cannula (94) visually, and perhaps physically, provide a means to locate depth stop device (95) of FIG. 1.

Obturator (92) of the present example incorporates a number of components with corresponding features. For instance, obturator (92) includes a shaft (214) that includes fluid lumen (216) that communicates between imageable side notch (218) and proximal port (220). Shaft (214) is longitudinally sized such that piercing tip (222) extends out of distal end (202) of cannula (94). Obturator thumbwheel cap (224) encompasses proximal port (220) and includes locking feature (226), which includes visible angle indicator (228), that engages cannula thumbwheel (204) to ensure that imageable side notch (218) is registered to lateral aperture (201) in cannula (94). Obturator seal cap (230) may be engaged proximally into obturator thumbwheel cap (224) to close fluid lumen (216). Obturator seal cap (230) of the present example includes locking or locating feature (232) that includes visible angle indicator (233) that corresponds with visible angle indicator (228) on obturator thumbwheel cap (224), which may be fashioned from either a rigid, soft, or elastomeric material. In FIG. 9, guide cube (104) has guided obturator (92) and cannula (94) through grid plate (96).

While obturator (92) of the present example is hollow, it should be understood that obturator (92) may alternatively have a substantially solid interior, such that obturator (92) does not define an interior lumen. In addition, obturator (92) may lack side notch (218) in some versions. Other suitable components, features, configurations, functionalities, operability, etc. for an obturator (92) will be apparent to those of ordinary skill in the art in view of the teachings herein. Likewise, cannula (94) may be varied in a number of ways. For instance, in some other versions, cannula (94) has a closed distal end (202). As another merely illustrative example, cannula (94) may have a closed piercing tip (222) instead of obturator (92) having piercing tip (222). In some such versions, obturator (92) may simply have a blunt distal end; or the distal end of obturator (92) may have any other suitable structures, features, or configurations. Other suitable components, features, configurations, functionalities, operability, etc. for a cannula (94) will be apparent to those of ordinary skill in the art in view of the teachings herein. Furthermore, in some versions, one or both of obturator (92) or cannula (94) may be omitted altogether. For instance, needle (90) of probe (91) may be directly inserted into a guide cube (104), without being inserted into guide cube (104) via cannula (94).

Another component that may be used with probe (91) (or needle (90)) is depth stop device (95). Depth stop device (95) may be of any suitable configuration that is operable to prevent cannula (94) and obturator (92) (or needle (90)) from being inserted further than desired. For instance, depth stop device (95) may be positioned on the exterior of cannula (94) (or needle (90)), and may be configured to restrict the extent to which cannula (94) is inserted into a guide cube. It should be understood that such restriction by depth stop device (95) may further provide a limit on the depth to which the combination of cannula (94) and obturator (92) (or needle (90)) may be inserted into the patient's breast. Furthermore, it should be understood that such restriction may establish the depth within the patient's breast at which biopsy device (14) acquires one or more tissue samples after obturator (92) has been withdrawn from cannula (94) and needle (90) has been inserted in cannula (94). Exemplary depth stop devices (95) that may be used with biopsy system (10) are described in U.S. Pub. No. 2007/0255168, entitled "Grid and Rotatable Cube Guide Localization Fixture for Biopsy Device," published Nov. 1, 2007, and incorporated by reference herein as mentioned previously.

In the present example, and as noted above, biopsy device (14) includes a needle (90) that may be inserted into cannula (94) after the combination of cannula (94) and obturator (92) has been inserted to a desired location within a patient's breast and after obturator (92) has been removed from cannula (94). Needle (90) of the present example comprises a lateral aperture (not shown) that is configured to substantially align with lateral aperture (201) of cannula (94) when needle (90) is inserted into lumen (196) of cannula (94). Probe (91) of the present example further comprises a rotating and translating cutter (not shown), which is driven by components in holster (32), and which is operable to sever tissue protruding through lateral aperture (201) of cannula (94) and the lateral aperture of needle (90). Severed tissue samples may be retrieved from biopsy device (14) in any suitable fashion.

It should be understood that although biopsy system (10) is discussed above as utilizing disposable probe assembly (91), other suitable probe assemblies and biopsy device assemblies may be utilized. By way of example only, other suitable biopsy devices may be configured and operable in accordance with at least some of the teachings of U.S. Pat. No. 8,206,316, entitled "Tetherless Biopsy Device with Reusable Portion," issued Jun. 26, 2012, the disclosure of which is incorporated by reference herein; U.S. Pat. No. 8,277,394, entitled "Multi-Button Biopsy Device," issued Oct. 2, 2012, the disclosure of which is incorporated by reference herein; and/or U.S. Pub. No. 2012/0065542, entitled "Biopsy Device Tissue Sample Holder with Removable Tray," published Mar. 15, 2012, the disclosure of which is incorporated by reference herein. As yet another merely illustrative example, other suitable biopsy devices may be configured and operable in accordance with at least some of the teachings of U.S. Pub. No. 2010/0160824, the disclosure of which is incorporated by reference herein; U.S. Patent Pub. No. 2013/0144188, entitled "Biopsy Device with Slide-In Probe," published Jun. 6, 2013, the disclosure of which is incorporated by reference herein; U.S. Patent Pub. No. 2013/0324882, entitled "Control for Biopsy Device," published Dec. 5, 2013, the disclosure of which is incorporated by reference herein; U.S. Patent Pub. No. 2014/0039343, entitled "Biopsy System," published Feb. 6, 2014, the disclosure of which is incorporated by reference herein; and/or U.S. Patent Pub. No. 2015/0065913, entitled "Tissue Collection Assembly for Biopsy Device," published Mar. 5, 2015, the disclosure of which is incorporated by reference herein.

Still other suitable forms of biopsy devices that may be used in conjunction with the various alternative components of system (10) as described herein will be apparent to those of ordinary skill in the art.

IV. EXEMPLARY GUIDE CUBE

In some versions, a guide cube may comprise a body defined by one or more edges and faces. The body may include one or more guide holes or other types of passages that extend between faces of the guide cube and that may be used to guide an instrument such as a biopsy device (14) or a portion of a biopsy device (14) (e.g., needle (90) of biopsy device (14), a combination of cannula (94) and obturator (92), etc.). Guide cubes may be rotatable about one, two, or three axes to position the one or more guide holes or passages of the guide cube into a desired position.

Figure 4:
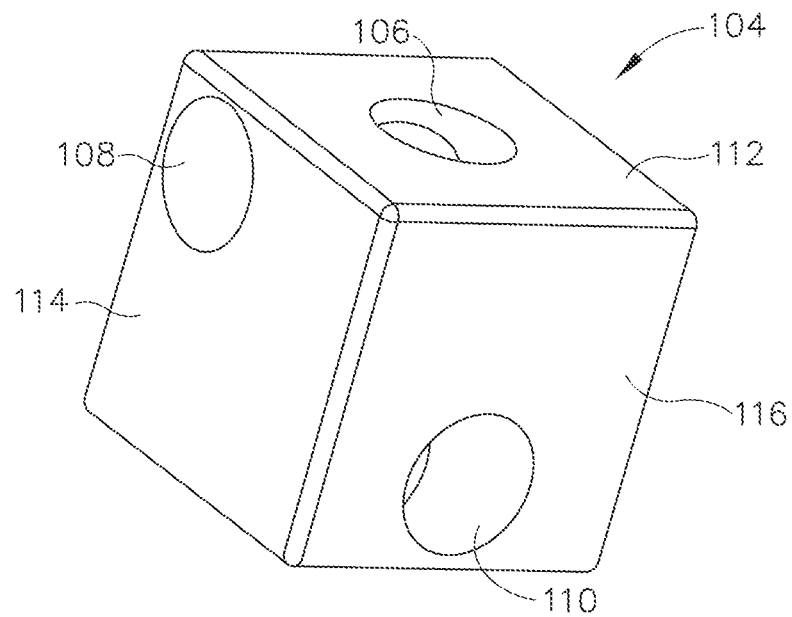
FIG. 4 depicts a perspective view of a two-axis rotatable guide cube of the biopsy system of FIG. 1.
Figure 5:
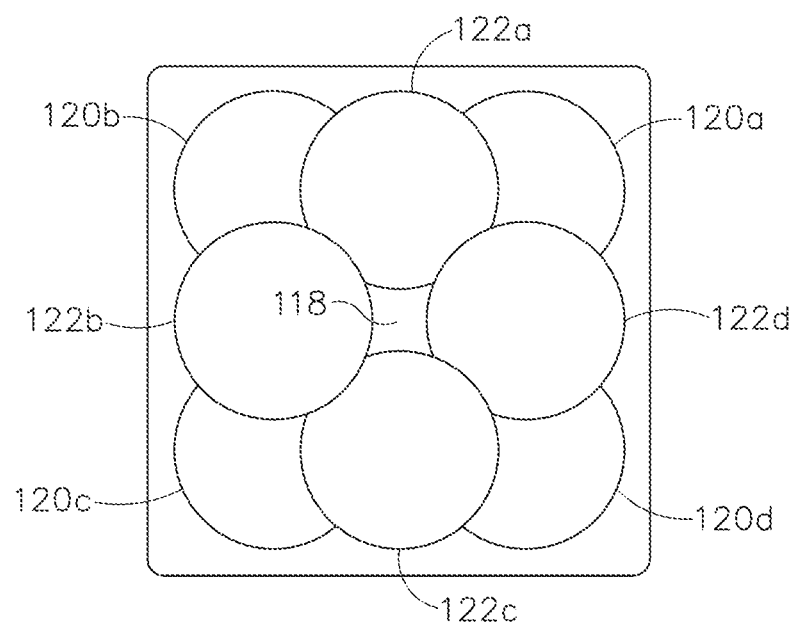
FIG. 5 depicts a diagram of nine guide positions achievable by the two-axis rotatable guide cube of FIG. 4.

In FIG. 4, guide cube (104) includes a central guide hole (106), a corner guide hole (108), and an off-center guide hole (110) that pass orthogonally to one another between respective opposite pairs of faces (112, 114, 116). By selectively rotating guide cube (104) in two axis, one of pairs of faces (112, 114, 116) may be proximally aligned to an unturned position and then selected proximal face (112, 114, 116) optionally rotated a quarter turn, half turn, or three-quarter turn. Thereby, one of nine guide positions (118) (i.e., using central guide hole (106)), (120a-120d) (i.e., corner guide hole (108)), (122a-122d) (i.e., using off-center guide hole (110)) may be proximally exposed as depicted in FIG. 5.

Figure 6:
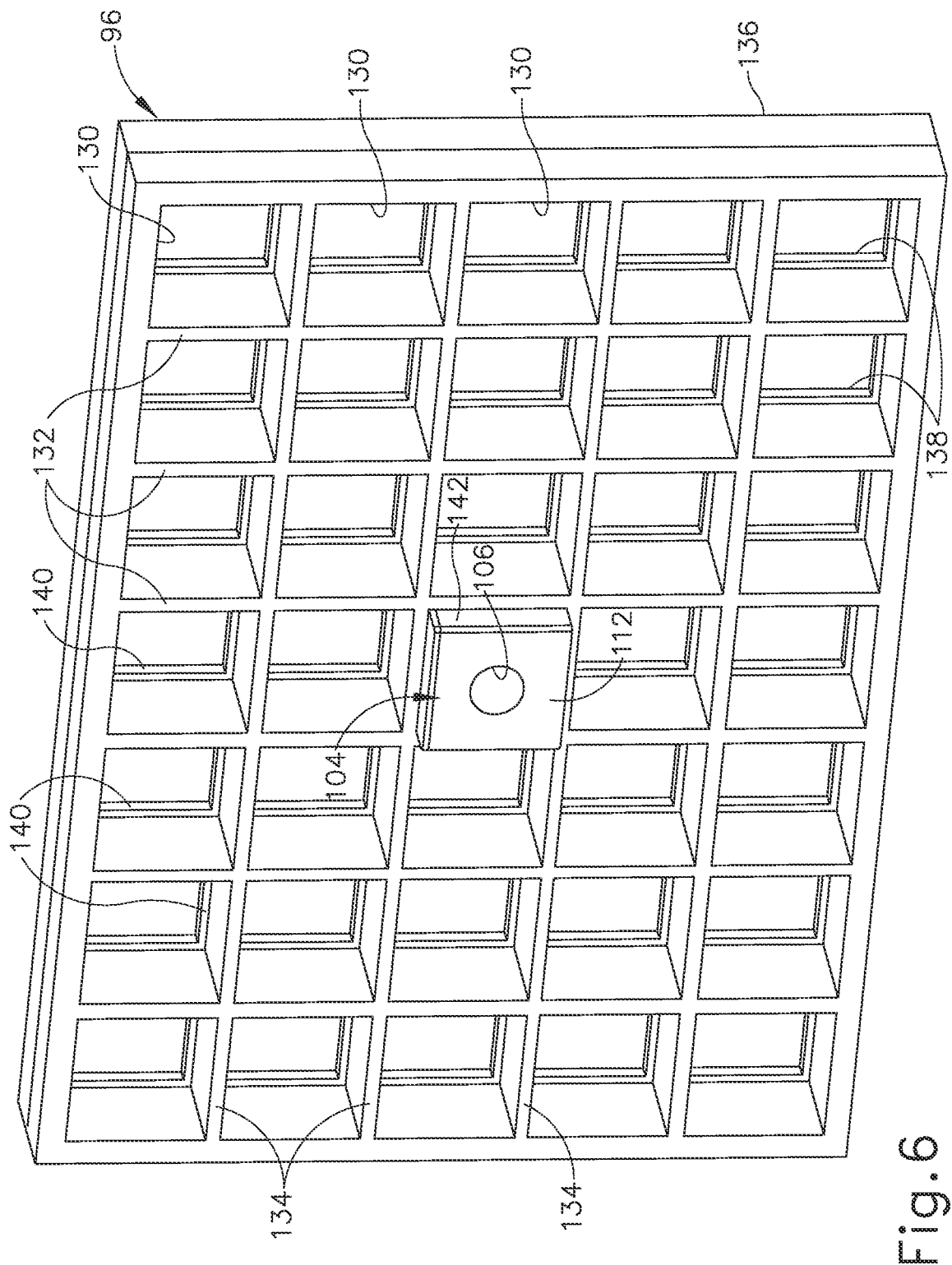
FIG. 6 depicts a perspective view of a two-axis rotatable guide cube into a lateral grid with the backing of the localization fixture of FIG. 1.

In FIG. 6, two-axis rotatable guide cube (104) is sized for insertion from a proximal side into one of a plurality of square recesses (130) in grid plate (96), which are formed by intersecting vertical bars (132) and horizontal bars (134). Guide cube (104) is prevented from passing through grid plate (96) by backing substrate (136) attached to a front face of grid plate (96). Backing substrate (136) includes respective square opening (138) centered within each square recess (130), forming lip (140) sufficient to capture the front face of guide cube (104), but not so large as to obstruct guide holes (104, 106, 108). The depth of square recesses (130) is less than guide cube (104), thereby exposing a proximal portion (142) of guide cube (104) for seizing and extraction from grid plate (96). It will be appreciated by those of ordinary skill in the art based on the teachings herein that backing substrate (136) of grid plate (96) may be omitted altogether in some versions. In some such versions without backing substrate (136) other features of a guide cube, as will be discussed in more detail below, may be used to securely and removably fit a guide cube within a grid plate. However, such other features may also be used in combination with a grid plate having backing substrate (136), such as grid plate (96), instead of partially or wholly omitting backing substrate (136).

In some other versions, guide cube (104) is replaced with an alternative guide cube or other guide structure that is configured and operable in accordance with at least some of the teachings of U.S. patent application Ser. No. 14/335,051, entitled "Biopsy Device Targeting Features," filed Jul. 18, 2014, the disclosure of which is incorporated by reference herein.

V. EXEMPLARY ALTERNATIVE TARGETING SET WITH ADJUSTABLE OBTURATOR

As described above with respect to targeting set (89), it is generally desirable to adjust the extension of obturator (92) and cannula (94) relative to a fixed reference point. In the examples described above, this adjustability is accomplished through the use of depth stop device (95), which is selectively securable to cannula (94) at various axial positions along the length of cannula (94). As described above, when used in conjunction with guide cube (104), depth stop device (95) is generally usable to control the depth of insertion of obturator (92) and cannula (94) into a patient.

Although the configuration of obturator (92), cannula (94), and depth stop device (95) described above is generally effective in a variety of circumstances, in some circumstances this configuration may lead to some of challenges. For instance, as described above, depth stop device (95) is securable to cannula (94) by rotating depth stop device (95) relative to cannula (94). While this method of securing depth stop device (95) is generally desirable, in some contexts, depth stop device (95) is used in confined spaces. In such contexts it may be challenging for an operator to successfully secure depth stop device (95) to cannula (94) because complete access to depth stop device (95) may be blocked by equipment, or other procedure room devices. Accordingly, in some circumstances it may be desirable to provide a targeting set similar to targeting set (89) described above with an alternative means for setting the depth of penetration of structures similar to obturator (92) and/or cannula (94).

In addition to the above, it may be also desirable to include certain features within a targeting set similar to targeting set (89) described above to improve the grip of structures similar to obturator (92) and/or cannula (94). For instance, some operators may have low strength relative to typical operators or may have smaller anatomical features (e.g., hands) relative to typical operators. Because penetration of tissue can sometimes require considerable force, certain operators may require additional gripping features to successfully pierce tissue using obturator (92) and/or cannula (94). Thus, in some circumstances it may be desirable to include certain features within a targeting set similar to targeting set (89) described above to improve the grip of structures similar to obturator (92) and/or cannula (94).

As a variation of obturator (92) and cannula (94) discussed above, various alterative obturators and/or cannulas may include additional features and/or components to permit alternative modes of setting the depth of penetration of the obturator and/or cannula. Such configurations may be desirable in confined spaces where structures similar to depth stop device (95) may be difficult to access. Among other benefits, such a configuration may improve the ease of use and/or operability of obturator (92) and/or cannula (94). Various examples of how obturator (92) and cannula (94) may be reconfigured to incorporate alternative modes of setting the depth of penetration are described below; while other examples will be apparent to those of ordinary skill in the art according to the teachings herein. It should be understood that the obturator and cannula examples described below may function substantially similar to obturator (92) and cannula (94) described above. In particular, the obturator and cannula examples described below may be used to assist in biopsy device needle targeting within a patient's breast using Mill guidance. It should be understood that the cannula tip examples discussed below may be used with any of the biopsy devices discussed above or disclosed herein.

It should also be understood that the teachings below may be readily combined with the teachings of U.S. Pat. Pub. No. 2015/0025414, entitled "Biopsy Device Targeting Features," published Jan. 22, 2015, the disclosure of which is incorporated by reference herein. In other words, the various cannulas and obturators described in U.S. Pat. Pub. No. 2015/0025414 may be modified in accordance with at least some of the teachings herein in numerous ways as will be apparent to those of ordinary skill in the art in view of the teachings herein. Similarly, the various examples of cannulas and obturators described herein may be modified in accordance with at least some of the teachings in U.S. Pat. Pub. No. 2015/0025414 in numerous ways as will be apparent to those of ordinary skill in the art in view of the teachings herein. Additionally, or in the alternative, the various examples of cannulas and obturators described herein may be modified in accordance with at least some of the teachings in U.S. Pat. App. No. 62/157,586, entitled "Mill Guided Biopsy Targeting Assembly with Obturator Overshoot Feature," filed May 6, 2015, the disclosure of which is incorporated by reference herein.

Figure 10:
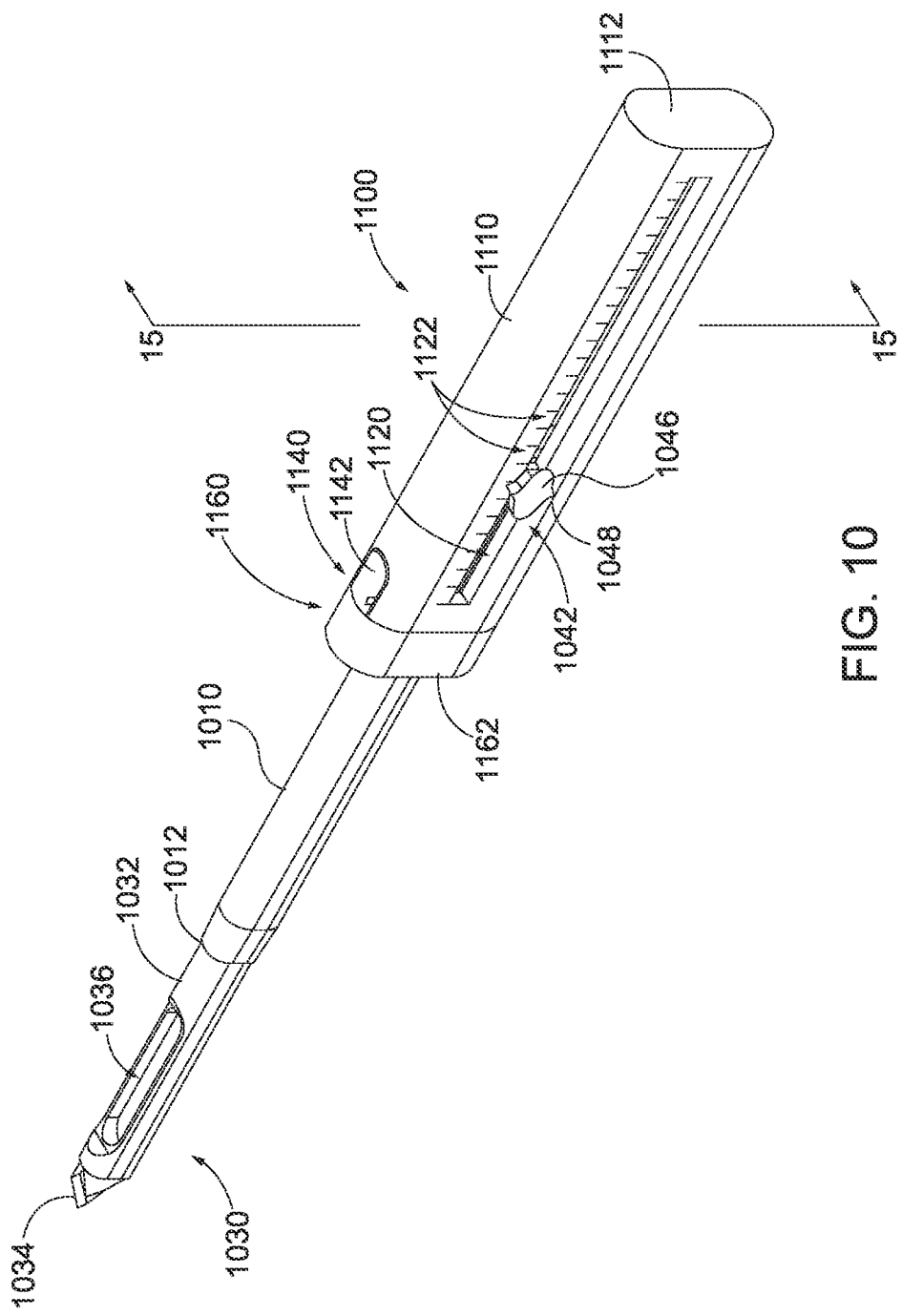
FIG. 10 depicts a perspective view of an exemplary alternative targeting set for use with the biopsy system of FIG. 1.
Figure 11:
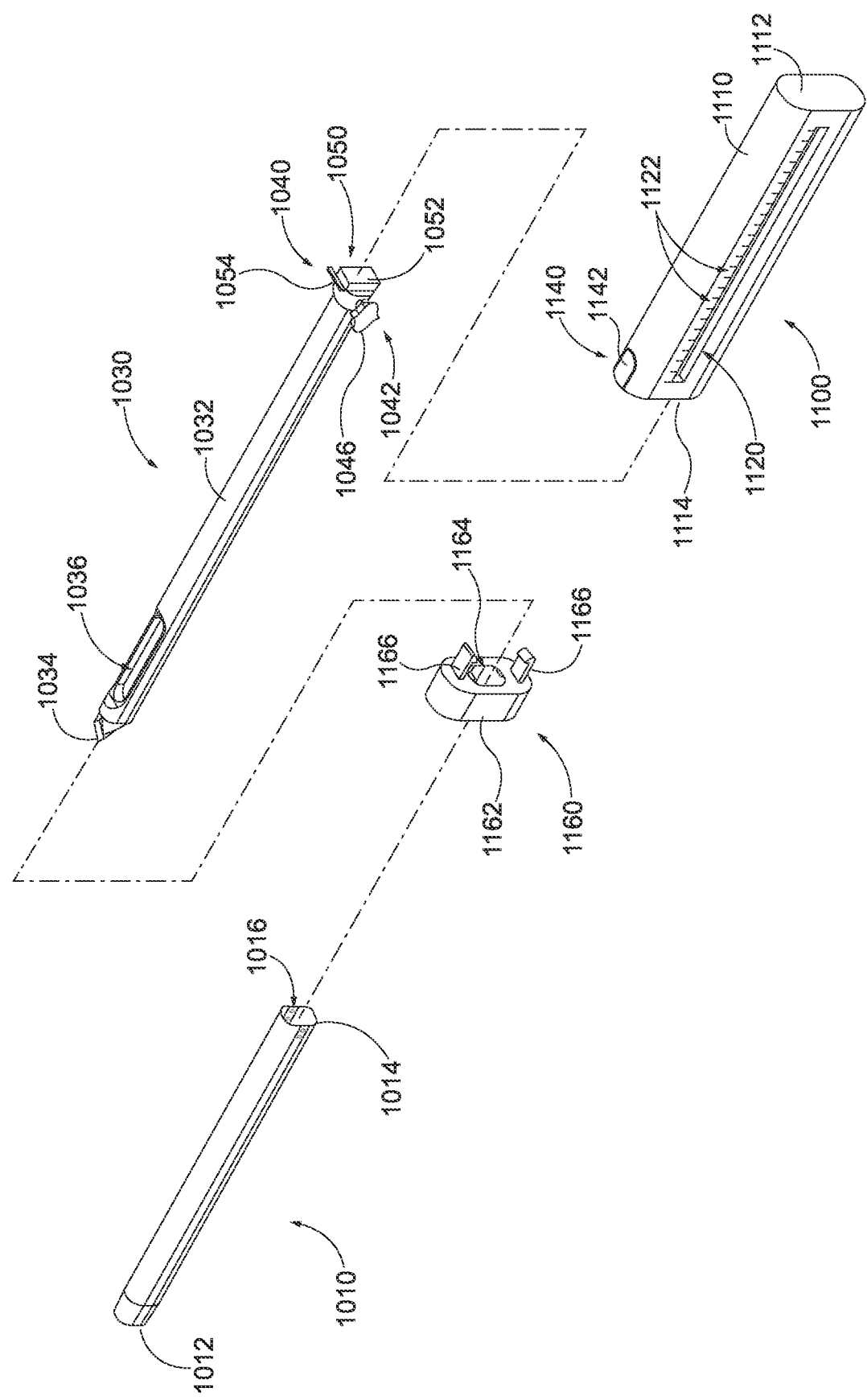
FIG. 11 depicts a perspective exploded view of the targeting set of FIG. 10.

FIGS. 10 and 11 show an exemplary alternative targeting set (1000) for use in association with probe (91) as similarly described above with respect to targeting set (89). Like with targeting set (89), targeting set (1000) of the present example comprises a cannula (1010) and a stylet or obturator (1030). However, unlike targeting set (89) described above, targeting set (1000) of the present example includes an obturator actuation assembly (1100). As will be described in greater detail below, targeting set (1000) is generally configured such that obturator (1030) and cannula (1010) are actuatable relative a depth stop (1160). Although targeting set (1000) is described herein as being usable with cannula (1010), it should be understood that cannula (1010) in the present example may be omitted entirely in some examples. In such examples, obturator (1010) and components associated with obturator (1010) generally operate in substantially the same way unless otherwise noted herein. In still other examples, cannula (1010) can alternatively be replaced with cannula (94) described above.

Figure 12:
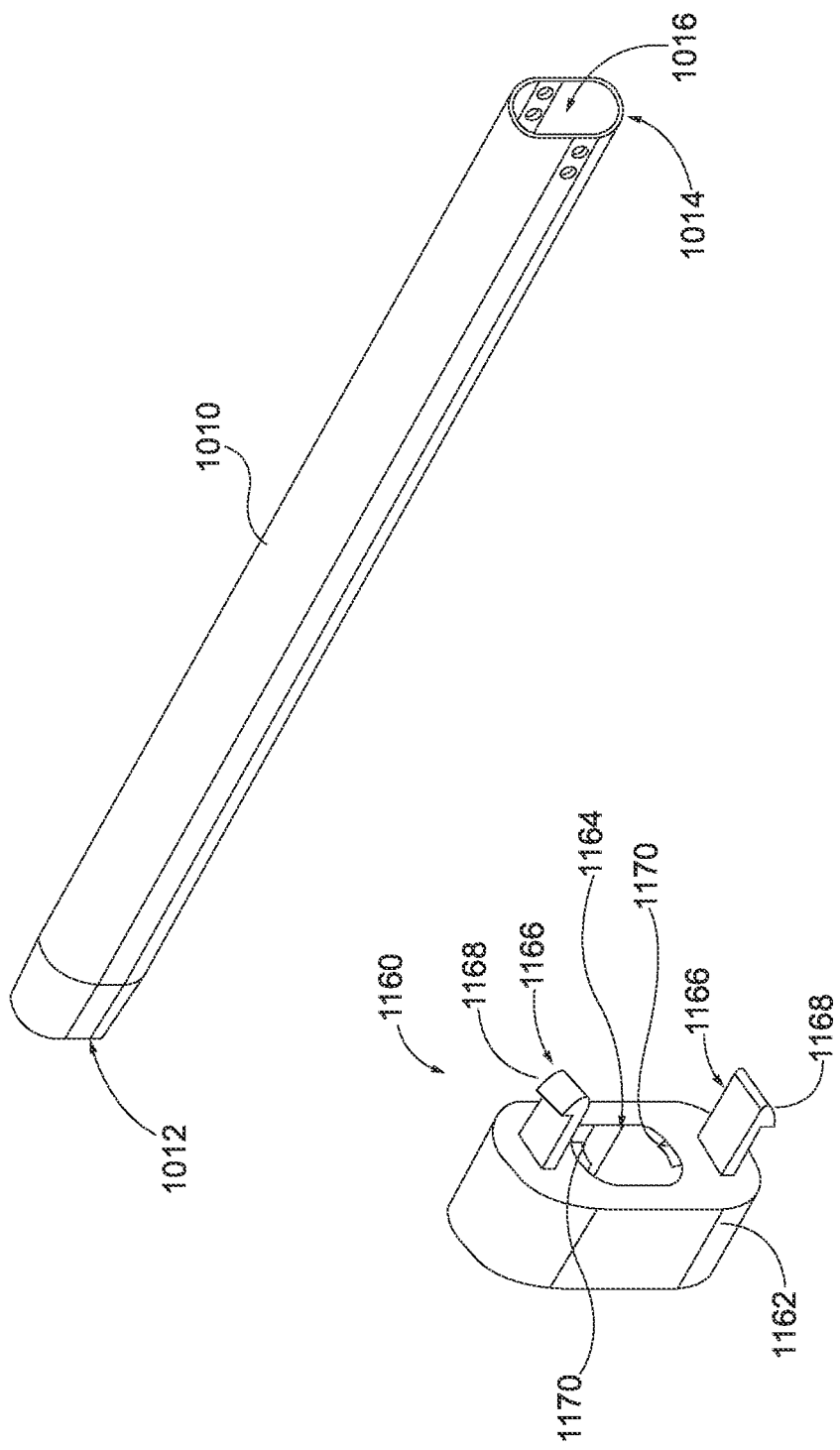
FIG. 12 depicts a perspective view of a cannula and depth stop of the targeting set of FIG. 10.

As best seen in FIG. 12, cannula (1010) of the present example defines a lumen (1016) and includes an open distal end (1012) and an open proximal end (1014). In the present example, at least a portion of cannula (1010) is tapered adjacent to open distal end (1012). Such a taper may be desirable to reduce the force required to penetrate tissue by reducing the transition between obturator (1030) can cannula (1010). In other examples, such a taper is merely optional and can be omitted.

Although not shown, it should be understood that in some cannula (1010) includes a lateral aperture adjacent to open distal end (1012). In such examples, the lateral aperture can be in communication with lumen (1016) to communicate fluids, tissue samples, and/or other biopsy procedure related materials through the exterior of cannula (1010) and into the interior of cannula (1010). In addition, cannula (1010) may also be equipped with a hub or other structure that can include ports in communication with lumen (1016). In examples that include ports, such ports may be optionally coupled to a fluid source for delivery of therapeutic substances, saline, or other fluids to a biopsy site via lumen (1016). Examples that include structures similar to a hub can also include other features and/or components such as seals, thumbwheels, fluid channels, and/or additional lumen similar to cylindrical hub (198) described above.

FIG. 12 also shows depth stop (1160) in greater detail. As can be seen, depth stop (1160) comprises an oval-shaped body (1162) defining a cannula opening (1164) extending transversely through body (1162). As will be described in greater detail below, depth stop (1160) is generally configured to receive cannula (1010) via cannula opening (1164) to thereby provide an interface between obturator actuation assembly (1100) and guide cube (104). However, it should be understood that unlike depth stop device (95) described above, depth stop (1160) can generally permit at least some movement of cannula (1010) relative to depth stop (1160). As will be described in greater detail below, movement of cannula (1010) relative to depth stop (1160) can still be generally restricted to some degree.

Depth stop (1160) further includes one or more attachment tabs (1166) extending proximally from body (1160). Each attachment tab (1166) includes an outwardly projecting tooth (1168). As will be described in greater detail below, each tooth (1168) of each attachment tab (1166) is generally configured to engage at least a portion of obturator actuation assembly (1100) to selectively lock depth stop (1160) to obturator actuation assembly (1100).

Depth stop (1160) further includes a pair of cannula stops (1170) projecting into cannula opening (1164) from body (1162). Each cannula stop (1170) projects from an opposite face of cannula opening (1164) such that each cannula stop (1170) is configured to apply an opposing force to cannula (1010) when cannula (1010) is disposed within depth stop (1160). Each cannula stop (1170) also projects distally into cannula opening (1164) such that each cannula stop (1170) is oriented at an angle relative to an axis defined by the extension of cannula opening (1164) through body (1162). As will be described in greater detail below, this configuration of cannula stops (1170) permits cannula stops (1170) to act as a one-way locking mechanism when cannula (1010) is inserted into depth stop (1160). Thus, as will be understood, cannula (1010) is generally movable distally into cannula opening (1164), while proximal movement of cannula (1010) is prevented by cannula stops (1170).

In some examples, it may be desirable for depth stop (1160) to include a selective locking feature such that depth stop (1160) can selectively lock onto cannula (1010) to be at a fixed longitudinal position along the length of cannula (1010). In particular, in some examples depth stop (1160) can be configured such that each cannula stop (1170) is configured as a rib or blade that can dig into, cut into, or otherwise fasten to the surface of cannula (1010). In such examples, each cannula stop (1170) can be oriented at a "corner" of the oval-shape of cannula opening (1164). In this position, each cannula stop (1170) is generally disengaged when the oval-shape of cannula opening (1164) is aligned with the oval-shape of cannula (1010). However, upon rotation of depth stop (1160) relative to cannula (1010), each cannula stop (1170) will engage cannula (1010) to lock depth stop (1160) at a desired position along the length of cannula (1010).

In examples such as the one described above where depth stop (1160) is rotated to lock to cannula (1010) it may also be desirable to replace attachment tabs (1166) with an alternative coupling mechanism to promote rotatable decoupling from obturator actuation assembly (1100). For instance, in some examples it may be desirable to use the rotation of depth stop (1160) that is used to lock depth stop (1160) to cannula (1010) to also disengage depth stop (1160) from obturator actuation assembly (1100). By way of example only, in some examples each attachment tab (1166) can be replaced with a shaft having a flange on the end opposite of depth stop (1160). The flange can then be used to lock into a channel with a large opening on one end for receipt of the flange. Of course, various alternative rotatable couplings can be used. It should be also understood that in examples where a rotatable coupling is used, obturator (1030) may have a circular shape while cannula (1010) may have an oval-shape. The circular shape of obturator (1030) in this example can permit relative rotation between cannula (1010) and obturator (1030) to promote rotational de-coupling.

Obturator (1030) of the present example comprises a rigid elongate shaft (1032) having a sharp distal tip (1034) and an oval-shaped transverse cross-section. Shaft (1032) of the present example comprises a single MRI compatible material such as ceramic or plastic, although no such limitation is intended. For instance, in other examples shaft (1032) comprises a non-MRI compatible material such as metal. However, in such examples, obturator (1030) may be removed from cannula (1010) during an MRI imaging procedure.

Shaft (1032) further includes a lateral aperture (1036) oriented proximally of the sharp distal tip (1034). Lateral aperture (1036) is positioned on shaft (1032) to be unobstructed by cannula (1010) when obturator (1030) is fully inserted into cannula (1010). Lateral aperture (1036) extends laterally into shaft (1032) to thereby form a chamber, notch, or recess in shaft (1032). As will be described in greater detail below, this configuration permits lateral aperture (1036) of obturator (1030) to receive tissue therein to thereby provide MRI visualization of the position of lateral aperture (1036) when obturator (1030) and cannula (1010) are disposed within a patient. Although not shown, it should be understood that in some examples shaft (1032) may include one or more lumens extending from lateral aperture (1036) to the proximal end of shaft (1032). When shaft (1032) is equipped with such lumens, the lumens can permit an operator to communicate fluid to or from lateral aperture (1036). Of course, such lumens are merely optional and in some examples shaft (1032) is merely solid with the exception of the chamber, recess, or notch formed by lateral aperture (1036). In addition, it should be understood that in some examples lateral aperture (1036) can be omitted entirely and shaft (1036) can therefore be completely solid. In such examples, obturator (1030) is used only to penetrate tissue, while a separate imaging element may be used in place of obturator (1030) once obturator (1030) is removed from cannula (1010). This separate imaging element can then be used to aid in visualizing lateral aperture (1016) of cannula (1010).

Figure 13:
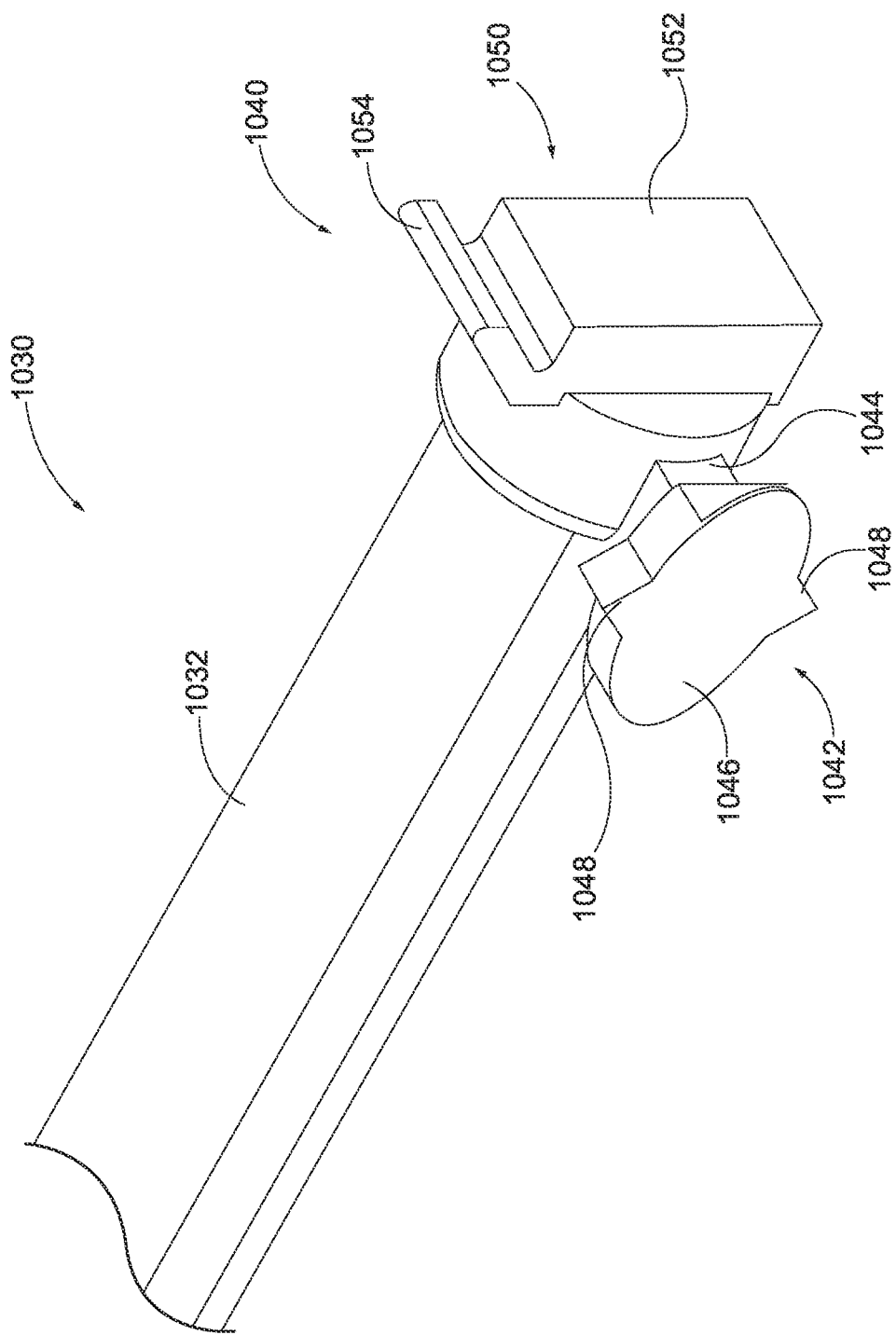
FIG. 13 depicts a detailed perspective view of an obturator of the targeting set of FIG. 10.

FIG. 13 shows obturator (1030) in greater detail. As can be seen, obturator (1030) further includes an actuator (1040) disposed on the proximal end of shaft (1032). As will be described in greater detail below, actuator (1040) is generally configured to engage at least a portion of obturator actuation assembly (1100) to selectively secure obturation (1030) in a plurality of predetermined positions relative to obturator actuation assembly (1100).

Actuator (1040) includes a manipulator portion (1042) and a lock portion (1050). In the present example, manipulation portion (1042) is positioned on a single side of shaft (1032). However, it should be understood that in some examples, obturator (1030) can include two opposing manipulation portions (1042) extending outwardly from opposite sides of shaft (1032).

Manipulation portion (1042) includes an arm (1044) and a grip (1046). Arm (1044) extends transversely from shaft (1032) and defines a generally rectangular shape, although other shapes may be used. Grip (1046) is disposed on the outermost end of arm (1044). Grip (1046) generally defines an oval shape. Two indicators (1048) extend upwardly and downwardly relative to the oval shape of grip. Indicators (1048) generally triangular in shape. As will be described in greater detail below, indicators (1048) are generally configured to provide an indication of the positioning of obturator (1030) relative to obturator actuation assembly (1100).

Arm (1044) extends from shaft (1032) to provide at least some separation of grip (1046) from shaft (1032). As will be described in greater detail below, the extension of arm (1044) is configured to permit arm (1044) to pass through at least a portion of obturator actuation assembly (1100). As will be understood, this is generally configured to provide access to grip (1046) such that an operator may manipulate grip (1046) to thereby manipulate obturator (1030).

Lock portion (1050) includes a rectangular body (1052) disposed on the proximal end of shaft (1032). Lock portion (1050) further includes a resilient stop (1054) extending upwardly from body (1052). In the present example, resilient stop (1054) is integral with body (1052) and defines a cross-section that is thin relative to body (1052). The thickness of resilient stop (1054) is generally configured to provide some stiffness to resilient stop (1054) such that resilient stop (1054) resists buckling along the axis of extension of resilient stop (1054). Resilient stop (1054) is also thin enough to such that resilient stop (1054) has some flexibility. Resilient stop (1054) is further oriented at an angle relative to body (1052). As will be described in greater detail below, this configuration generally permits resilient stop (1054) to lock the axial position of obturator (1030) in one direction relative to obturator actuation assembly (1100), while permitting axial movement of obturator (1030) relative to obturator actuation assembly (1100) when a predetermined axial force is applied to obturator (1030).

Figure 14:
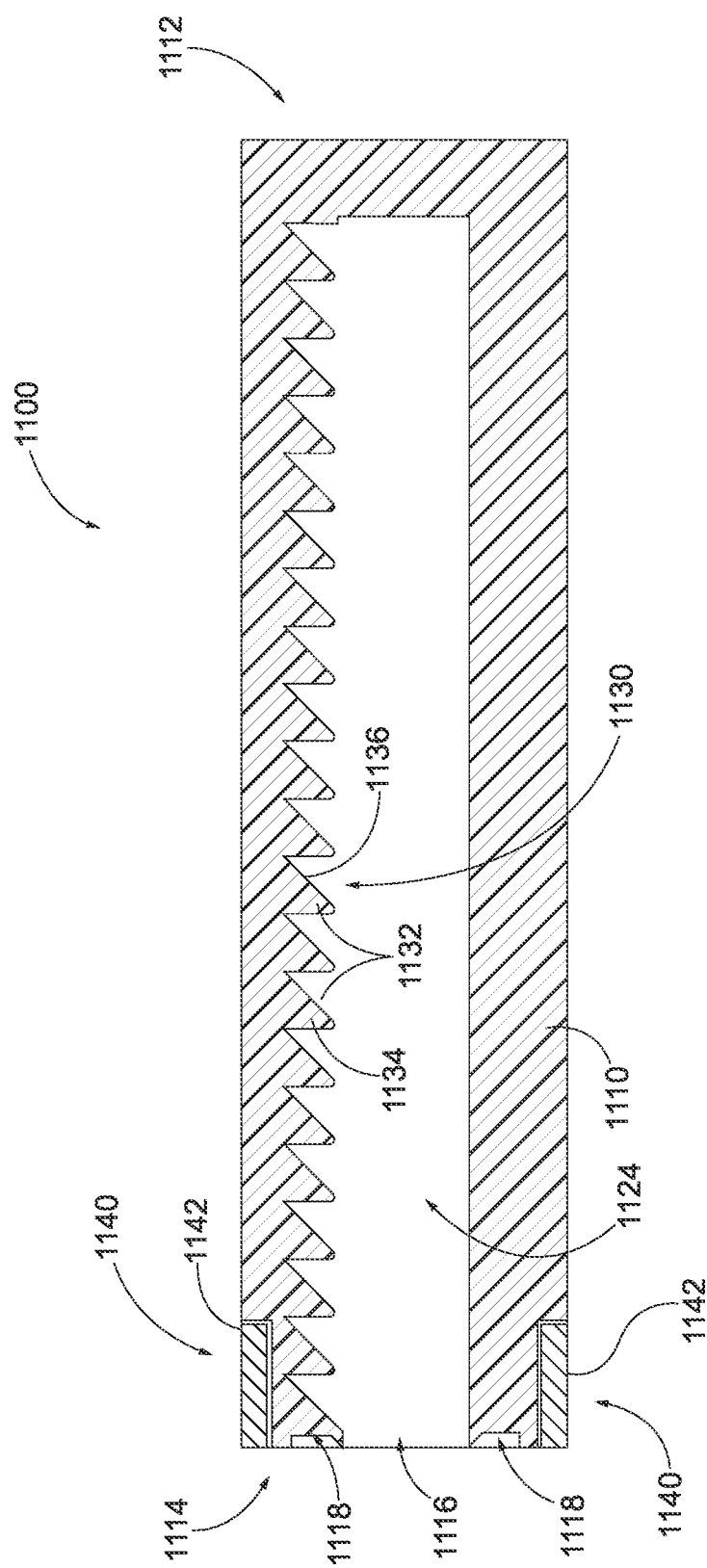
FIG. 14 depicts a side cross-sectional view of an obturator actuation assembly of the targeting set of FIG. 10.

FIGS. 10 and 14 show obturator actuation assembly (1100) in greater detail. As can be seen, obturator actuation assembly (1100) generally comprises an outer housing (1110), a lock array (1130), and a release mechanism (1140). Housing (1110) defines a closed proximal end (1112), an open distal end (1114), and an actuator slot (1120) disposed between the proximal and distal ends (1112, 1114). Open distal end (1114) defines an opening (1116) that is generally configured to receive the combination of cannula (1010) and obturator (1030) therethrough. Open distal end (1114) further includes a pair of recesses (1118) disposed above and below opening (1116). As will be described in greater detail below, recesses (1118) are generally configured to receive at least a portion of depth stop (1160) to permit actuation of one or more components of depth stop (1160).

Housing (1110) further defines a hollow interior (1124). Hollow interior (1124) is in communication with both opening (1116) defined by open distal end (1114) and actuation slot (1120). Hollow interior (1124) is defined by housing (1110) from open distal end (1114) to closed proximal end (1112). As will be described in greater detail below, this configuration permits obturator (1030) and cannula (1010) to move axially relative to housing (1110) from a position adjacent to closed proximal end (1112) to a position adjacent to open distal end (1114). To track the position of obturator (1030) within housing (1110), housing further includes indicia (1122) arranged in a linear pattern along the length of actuator slot (1120).

As best seen in FIG. 14, lock array (1130) is enclosed within hollow interior (1124) of housing (1110). Lock array (1130) is generally configured to engage at least a portion of obturator (1030) and thereby selectively secure obturator (1030) in a plurality of axial positions relative to obturator actuation assembly (1100). Although lock array (1130) of the present example is shown as being integral with housing (1110), it should be understood that in other examples lock array (1130) can be configured as a separate component attached to housing (1110).

Lock array (1130) comprises of teeth (1132) extending downwardly from housing (1110) into hollow interior (1124). Teeth (1132) are arranged in a linear pattern extending between closed proximal end (1112) and open distal end (1114) within hollow interior (1124). Each tooth (1132) forms a shape corresponding to a right triangle. Thus, each tooth (1132) includes a flat leg (1134) and an angled leg (1136). As will be described in greater detail below, the flat leg (1134) and angled leg (1136) configuration of each tooth (1132) is configured to permit lock array (1130) to generally act as a ratchet mechanism relative to obturator (1030).

Release mechanism (1140) of obturator actuation assembly (1100) is configured to receive at least a portion of depth stop (1160) to selectively secure depth stop (1160) to obturation actuation assembly (1100). Release mechanism (1140) includes two buttons (1142) integrated into opposing sides of housing (1110). Although not shown, it should be understood that either housing (1110) or release mechanism (1140) can include ports, channels or other components configured to receive attachment tabs (1166) of depth stop (1160). Buttons (1142) are generally movable and/or pivotable to interact with attachment tabs (1166) when received within ports, or channels disposed within housing (1110) or release mechanism (1140). For instance, when buttons (1142) are in a relaxed state, buttons (1142) can secure or otherwise fasten attachment tabs (1166) relative to buttons (1142). Similarly, to release attachment tabs (1166), buttons (1142) can be pivoted or moved to disengage from attachment tabs (1166) and thereby release depth stop (1160) from obturator actuation assembly (1100). Although release mechanism (1140) is shown in the present example as having a pivotable or movable button (1142) configuration, it should be understood that in other examples various alternative mechanism for coupling depth stop (1160) to obturator actuation assembly (110) may be used as will be apparent to those of ordinary skill in the art in view of the teachings herein.

Figure 15A:
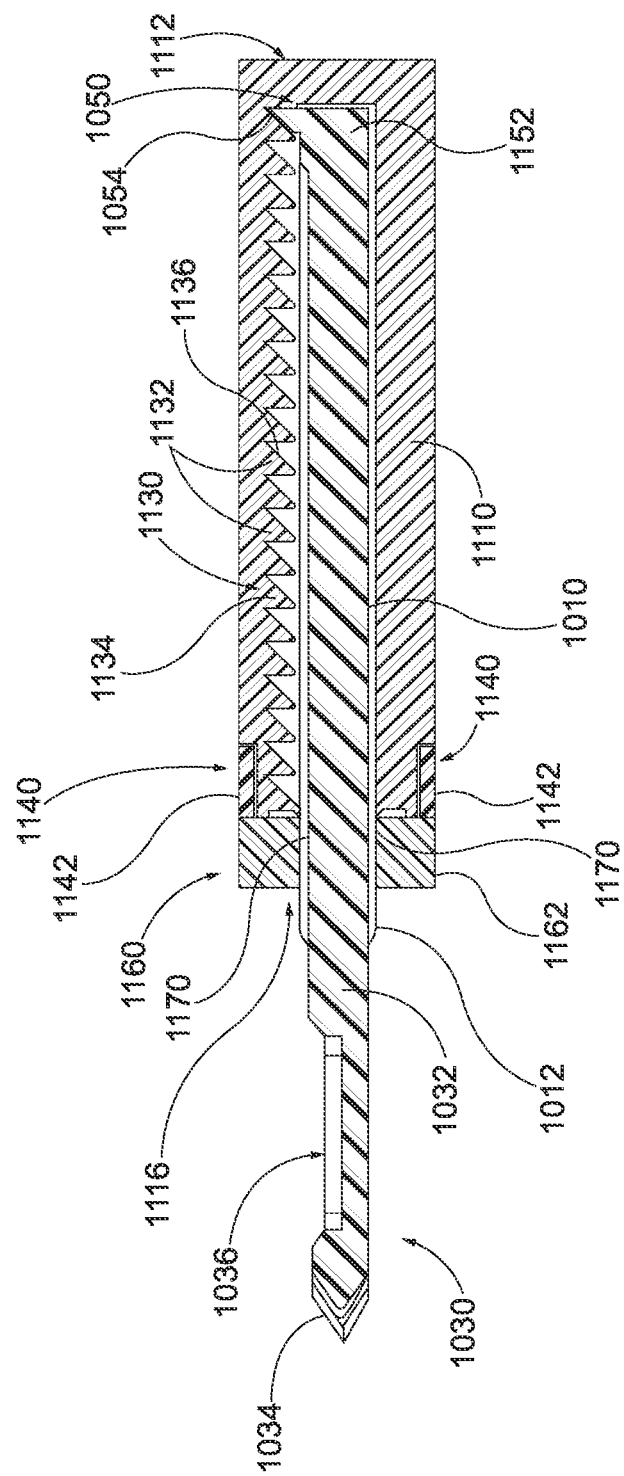
FIG. 15A depicts a side cross-sectional view of the targeting set of FIG. 10, the cross-section taken along line 15-15 of FIG. 10, with the obturator in an initial position.

FIG. 15A shows obturator (1030) disposed within obturator actuation assembly (1100). As can be seen, when obturator (1030) is disposed within obturator actuation assembly (1100), resilient stop (1054) of lock portion (1050) is disposed adjacent to a given angled leg (1136) of a particular tooth (1132) of lock array (1130). It should be understood that resilient stop (1054) is generally oriented at an angle that is substantially similar to the angle defined by angled leg (1136) of each tooth (1132) to permit resilient stop (1054) to nest adjacently relative to angled leg (1136). In this position, resilient stop (1054) is generally in a relaxed state. However, as will be described in greater detail below, if obturator (1030) is pushed distally, resilient stop (1054) is configured to flex downwardly via angled leg (1136) and underneath tooth (1132) to permit advancement of obturator (1030) relative to obturator actuation assembly (1100). Conversely, when obturator (1030) is pushed proximally, resilient stop (1054) bears against flat leg (1134) of a given tooth (1132) and therefore resists proximal movement of obturator (1030) relative to obturator actuation assembly (1100).

Figure 15B:
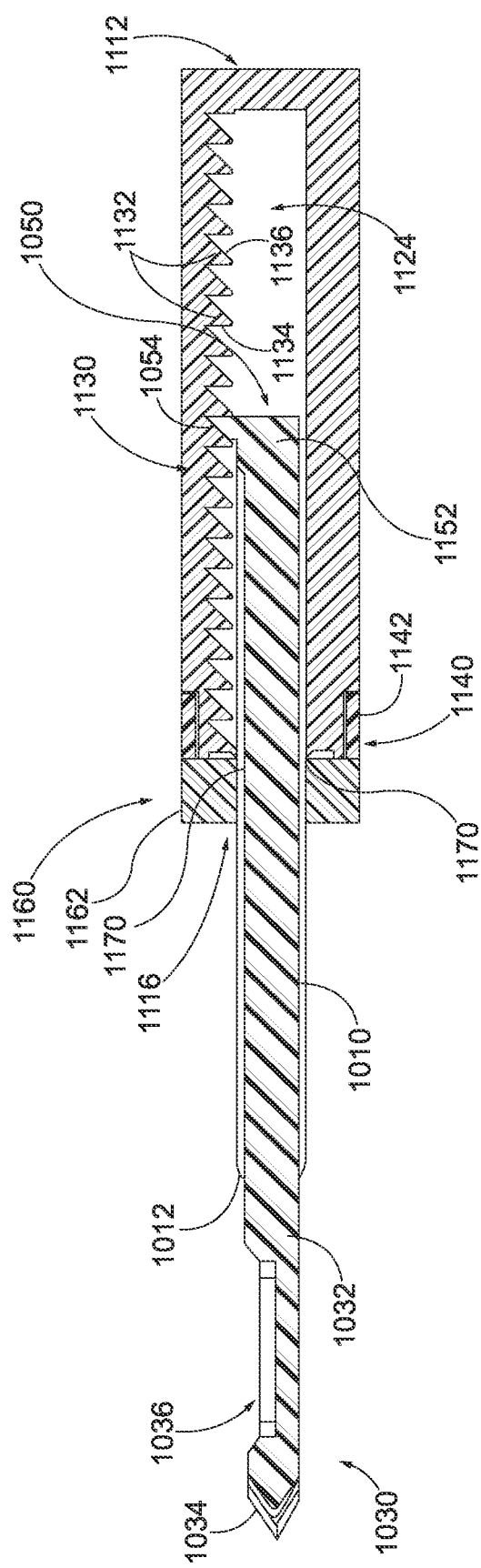
FIG. 15B depicts another side cross-sectional view of the targeting set of FIG. 10, with the obturator in an advanced position.

When obturator (1030) is disposed within obturation actuation assembly (1100), cannula (1010) can also be disposed within obturator actuation assembly (1100), as shown in FIG. 15. In particular, cannula (1010) is disposed coaxially around the exterior of obturator (1030). As obturator (1030) moves within obturation actuation assembly (1100), cannula (1010) likewise moves with obturator (1030). In the present example, cannula (1010) is pushed distally as obturator (1030) is pushed distally via engagement between open proximal end (1014) of cannula (1010) and arm (1044) of obturator (1030).

When both cannula (1010) and obturator (1030) are disposed within obturator actuation assembly (1100), depth stop (1160) can be secured to open distal end (1114) of housing (1110) via release mechanism (1140). Both cannula (1010) and obturator (1030) can thus pass through depth stop (1160), extending a predetermined length from depth stop (1160). In this configuration, cannula (1010) is at least partially held in an axial position by depth stop (1160). For instance, as described above, depth stop (1160) includes a pair of cannula stops (1170) that are configured to resiliently engage cannula (1010). Each cannula stop (1170) is oriented at a distally pointing angle. At this angle, each cannula stop (1170) permits relatively free distal translation of cannula (1010), yet generally prevents proximal movement. Thus, depth stop (1160) generally acts as a ratchet mechanism permitting distal advancement of cannula (1010), but substantially preventing proximal retraction of cannula (1010).

Figure 16:
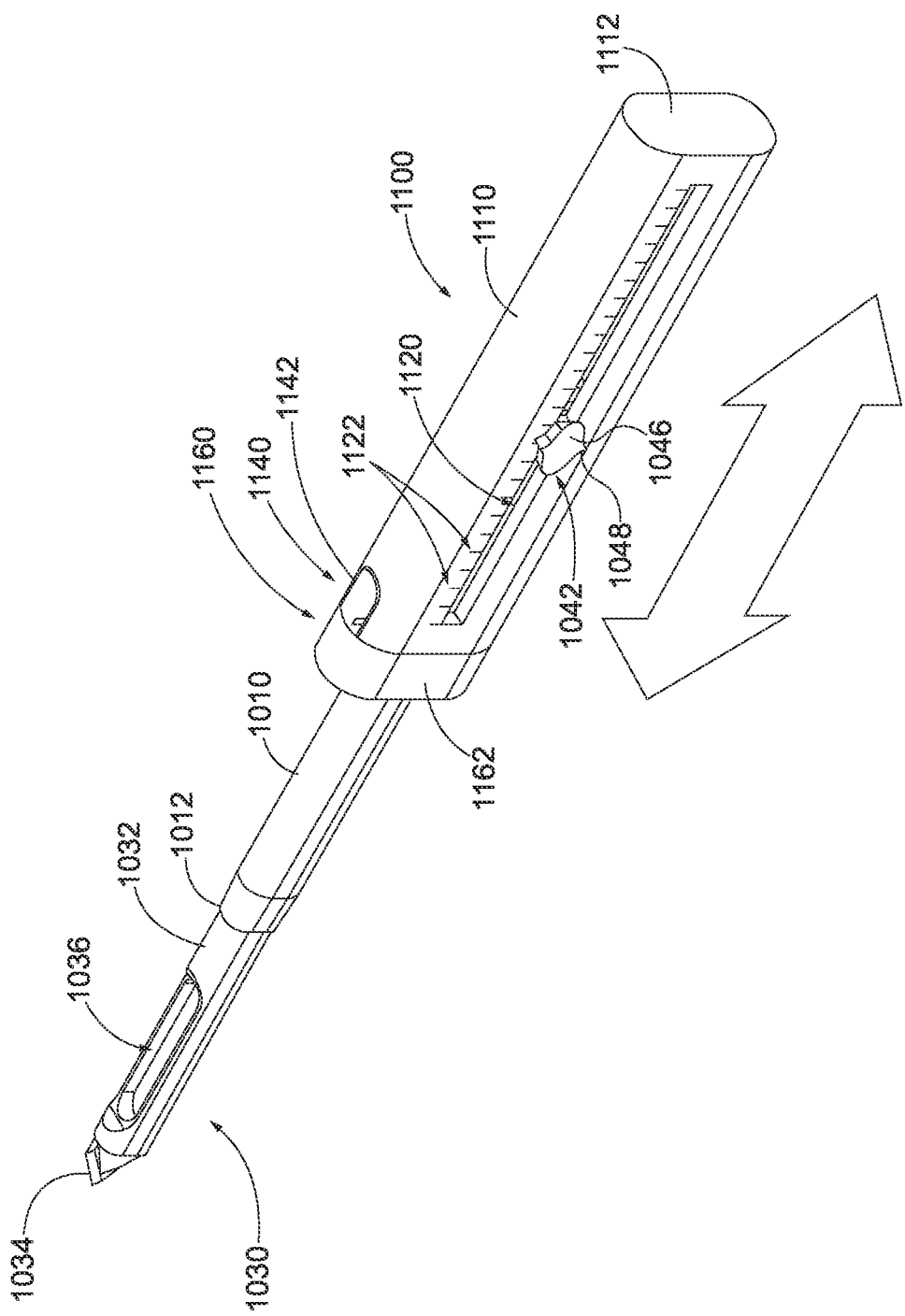
FIG. 16 depicts another perspective view of the targeting set of FIG. 10, with the obturator is the advanced position.

FIGS. 15A-16 show an exemplary use of targeting set (1000). As can be seen in FIG. 15A, targeting set (1000) is initially in an initial configuration. In the initial configuration, obturator (1030) and cannula (1010) are initially loaded within obturator actuation assembly (1100) with depth stop (1160) secured to open distal end (1114) of obturator actuation assembly (1100). Obturator (1030) and cannula (1010) are also positioned at an initial position relative to obturation actuation assembly (1100). In the initial position, obturator (1030) and cannula (1010) are retracted proximally relative to obturator actuation assembly (1100) at a proximal most position. Further proximal movement of obturator (1030) is blocked due to body (1052) of obturator (1030) being positioned adjacent to closed proximal end (1112) of obturator actuation assembly (1100).

In the present use, targeting set (1000) is supplied to an operator in the configuration shown in FIG. 15A. However, in other uses, targeting set (1000) can be supplied with cannula (1010), obturator (1030), obturator actuation assembly (1100), and depth stop (1160) separated from each other. In such a use, it should be understood that an operator may engage in some assembly prior to performing the procedure described herein.

Once targeting set (1000) is placed in the initial configuration described above, an operator can prepare targeting set (1000) for use in a biopsy procedure. To prepare targeting set (1000) for a biopsy procedure, an operator may grasp grip (1046) of obturator (1030) which protrudes from actuation slot (1120) of obturator actuation assembly (1100). An operator can subsequently use grip (1046) to translate obturator (1030) distally relative to obturator actuation assembly (1100). Obturator (1030) can be translated until obturator (1030) is set at a desired depth of penetration. To identify the desired depth of penetration, an operator can compare the position of indicators (1048) of obturator (1030) relative to indicia (1122) of obturator actuation assembly (1100).

It should be understood that as an operator adjusts obturator (1030), cannula (1010) translates along with obturator (1030) through engagement between open proximal end (1014) of cannula (1010) and arm (1044) of obturator (1030). Within obturator actuation assembly (1100), resilient stop (1054) moves within obturator actuation assembly (1100) from tooth (1132) to tooth (1132), thereby progressively locking obturator (1030) at a new axial position. Accordingly, it should be understood that once obturator (1030) is advanced to a given axial position, obturator (1030) cannot generally be retracted proximally. This feature may be desirable in some circumstances to prevent or discourage reuse of targeting set (1000) after a biopsy procedure. This feature is also desirable in some circumstances so that a force can be applied to housing of obturator actuation assembly (1100) to penetrate tissue using obturator (1030) without obturator (1030) collapsing proximally back into obturator actuation assembly (1100).

Once the desired depth of penetration of obturator (1030) is set using grip (1046), an operator may use targeting set (1000) in connection with guide cube (104) and grid plate (96) as similarly described above with respect to targeting set (89). It should be understood that during a procedure it may be desirable to remove obturator (1030) from cannula (1010) to use cannula (1010) for introducing biopsy device (10), marker delivery devices, or other medical instruments to the biopsy site. To remove obturator (1030), an operator can actuate buttons (1142) of release mechanism (1140) to disengage obturator actuation assembly (1100) from attachment tabs (1166) of depth stop (1160). Once released, both obturator (1030) and obturator actuation assembly (1100) can be removed. Meanwhile, cannula (1010) remains in place due to engagement between cannula stops (1170) of depth stop (1160) and cannula (1010).

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A targeting set for use with positioning a biopsy device within a patient, the targeting set comprising: (a) an obturator; and (b) an actuator, wherein the actuator includes: (i) a housing, (ii) a lock array extending inwardly within a hollow interior defined by the housing, wherein the obturator is configured for insertion into the housing of the actuator such that at least a portion of the obturator engages the lock array, wherein the lock array is configured to selectively lock the obturator in a plurality of axial positions relative to the housing.

Example 2

The targeting set of Example 1, wherein the lock array defines a ratchet mechanism configured to permit distal advancement of the obturator relative to the housing, while preventing substantial proximal movement of the obturator relative to the housing.

Example 3

The targeting set of Examples 1 or 2, wherein the lock array includes a plurality of teeth, wherein each tooth of the plurality of teeth defines a flat portion and an angled portion.

Example 4

The targeting set of Example 3, wherein the obturator includes a resilient stop, wherein the resilient stop is configured to flex upon engagement with an angled portion of any one of the plurality of teeth.

Example 5

The targeting set of Example 4, wherein the resilient stop is configured to arrest movement of the obturator upon engagement with a flat portion of any one of the plurality of teeth.

Example 6

The targeting set of any one or more of Examples 3 through 5, further comprising a cannula, wherein the cannula is configured to coaxially receive the obturator.

Example 7

The targeting set of Example 6, wherein the obturator is configured to move the cannula as the obturator moves to an axial position relative to the housing.

Example 8

The targeting set Example 7, further comprising a depth stop, wherein the depth stop is configured to receive the cannula, wherein the depth stop is further configured to selectively attach to at least a portion of the housing.

Example 9

The targeting set of Example 8, wherein the obturator and the actuator are configured to detach from the cannula and the depth stop, wherein the cannula is configured to receive a biopsy instrument when the obturator and actuator are detached therefrom.

Example 10

The targeting set of Example 9, wherein the depth stop includes one or more cannula stops, wherein the one or more cannula stops are configured to permit distal movement of the cannula relative to the depth stop while substantially preventing proximal movement of the cannula relative to the depth stop.

Example 11

A biopsy system, comprising: (a) a biopsy device, wherein the biopsy device includes: (i) a body, (ii) a needle, and (iii) a cutter, wherein the needle extends from the body to collect tissue samples using the cutter; and (b) a targeting set, wherein the targeting set includes: (i) a cannula, (ii) an obturator having an elongate shaft and a sharp distal tip, and (iii) an obturator actuation assembly, wherein the cannula defines a lumen, wherein the lumen is configured to separately receive the needle of the biopsy device and the obturator, wherein the obturator actuation assembly is configured to permit distal translation of the obturator relative to at least a portion of the obturator actuation assembly to bias the obturator towards a plurality of axial positions.

Example 12

The biopsy system of Example 11, wherein the obturator actuation assembly is further configured to prevent the obturator from returning to a particular axial position of the plurality of axial positions once the obturator is advanced distally of the particular axial position.

Example 13

The biopsy system of Examples 11 or 12, wherein the obturator further includes a manipulator portion extending outwardly from the elongate shaft, wherein the obturator actuation assembly includes an outer housing defining a slot extending between a distal end and a proximal end of the outer housing, wherein the manipulator portion is configured to extend outwardly through the slot defined by the outer housing of the obturator actuation assembly.

Example 14

The biopsy system of Example 13, wherein the manipulation assembly of the obturator includes an arm and a grip, wherein the grip is configured for gasping by an operator to advance the obturator distally relative to the outer housing of the obturator actuation assembly.

Example 15

The biopsy system of Example 14, wherein the outer housing of the obturator actuation assembly defines a plurality of indicia arranged linearly along the slot defined by the outer housing, wherein the grip includes a plurality of indicators, wherein the indicia and the indicators are configured to together provide a penetration depth of the obturator.

Example 16

The biopsy system of any one or more of Examples 11 through 16, wherein the obturator further comprises a lock portion positioned on a proximal end of the elongate shaft, wherein the lock portion comprises a body and a resilient stop, wherein the resilient stop is configured to engage at least a portion of the obturator actuation assembly to bias the obturator towards the plurality of axial positions.

Example 17

The biopsy system of Example 16, wherein the resilient stop extends outwardly from the body at an angle relative to a lock axis, wherein the resilient stop is configured to flex when a force is applied to the resilient stop perpendicularly relative to the lock axis.

Example 18

The biopsy system of any one or more of Examples 11 through 18, further comprising a depth stop configured to receive the cannula, wherein the obturator actuation assembly includes a release mechanism, wherein the release mechanism is configured to engage the depth stop to selectively secure the depth stop to at least a portion of the obturator actuation assembly.

Example 19

The biopsy system of Example 18, wherein the release mechanism comprises one or more buttons, wherein each button of the one or more buttons is configured to pivot to thereby disengage from the depth stop.

Example 20

The biopsy system of Example 18, wherein the release mechanism is configured to disengage from the depth stop to permit removal of the obturator from the cannula for subsequent insertion of the needle of the biopsy device in to the cannula.

Example 21

A method for placing a targeting set at a biopsy site, wherein the targeting set includes an obturator and an obturator actuation assembly, wherein the method comprises: (a) grasping a housing of an obturator actuation assembly, the obturator actuation assembly having an obturator disposed therein at an initial position relative to the housing; (b) setting a depth of penetration by pushing the obturator distally relative to the housing of the obturator actuation assembly; and (c) inserting the obturator into tissue.

Example 22

The method of Example 21, wherein the obturator actuation assembly includes a lock array having a plurality of teeth, wherein the act of setting the depth of penetration includes moving the obturator to engage one or more teeth of the lock array.

Example 23

The method of Example 22, wherein the obturator engages a first tooth of the lock array when the obturator is in the initial position, wherein the obturator engages a second tooth of the lock array when setting the depth of penetration, wherein the second tooth is disposed distally of the first tooth.

Example 24

The method of Example 23, wherein the step of inserting the obturator into tissue includes resisting proximal movement of the obturator relative to the housing of the obturator actuation assembly via a tooth of the lock array.

Example 25

The method of any one or more of Examples 21 through 24, further comprising confirming the depth of penetration by observing the position of an indicator associated with the obturator with indicia defined by the housing of the obturator actuation assembly.

Example 26

The method of any one or more of Examples 21 through 25, further comprising detaching a depth stop from the obturator actuation assembly to remove the obturator and the obturator actuation assembly from a cannula disposed coaxially around the obturator.

Example 27

The method of any one or more of Examples 21 through 26, wherein the step of inserting the obturator into tissue is performed while grasping the housing of the obturator actuation assembly.

VII. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention.

Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A targeting set for use with positioning a biopsy device within a patient, the targeting set comprising:
   (a) a stylet;
   (b) a cannula, the cannula being configured to coaxially receive the stylet; and
   (c) an actuator, the actuator including:
      (i) a housing, and
      (ii) a lock array extending inwardly within a hollow interior defined by the housing, the stylet being configured for insertion into the housing of the actuator such that at least a portion of the stylet engages the lock array, the lock array being configured to selectively lock the stylet in a plurality of axial positions relative to the housing,
      the stylet being configured to move the cannula as the stylet moves to an axial position of the plurality of axial positions relative to the housing.

2. The targeting set of claim 1, the lock array defining a ratchet mechanism configured to permit distal advancement of the stylet relative to the housing, while preventing substantial proximal movement of the stylet relative to the housing.

3. The targeting set of claim 1, the lock array including a plurality of teeth, wherein each tooth of the plurality of teeth defines a flat portion and an angled portion.

4. The targeting set of claim 1, the lock array including a plurality of teeth; each tooth of the plurality of teeth defining a flat portion and an angled portion, the stylet including a resilient stop, the resilient stop being configured to flex upon engagement with an angled portion of any one of the plurality of teeth, the resilient stop being configured to arrest movement of the stylet upon engagement with a flat portion of any one of the plurality of teeth.

5. The targeting set of claim 1, the actuator including a slider positioned on an exterior of the housing and secured to the stylet to move the stylet relative to the housing, the housing including a plurality of depth indicators configured to indicate a depth of the stylet as the slider is moved relative to the housing.

6. The targeting set of claim 1, further comprising a depth stop, the depth stop being configured to receive the cannula, the depth stop being further configured to selectively attach to at least a portion of the housing.

7. The targeting set of claim 6, the stylet and the actuator being configured to detach from the cannula and the depth stop, the cannula being configured to receive a biopsy needle when the stylet and actuator are detached therefrom.

8. The targeting set of claim 6, the stylet and the actuator being configured to detach from the cannula and the depth stop, the cannula being configured to receive a biopsy needle when the stylet and actuator are detached therefrom, the depth stop including one or more cannula stops, the one or more cannula stops being configured to selectively lock into a desired longitudinal position along a length of the cannula.

9. A targeting set of use with positioning a biopsy device relative to a patient, the targeting set comprising:
   (a) a stylet; and
   (b) an actuator, the actuator including:
      (i) a housing, and
      (ii) a lock array extending inwardly within a hollow interior defined by the housing, the stylet being configured for insertion into the housing of the actuator such that at least a portion of the stylet engages the lock array, the lock array being configured to selectively lock the stylet in a plurality of axial positions relative to the housing,
   the lock array including a plurality of teeth, each tooth of the plurality of teeth defining a flat portion and an angled portion, the stylet including a resilient stop, the resilient stop being configured to flex upon engagement with an angled portion of any one of the plurality of teeth, the resilient stop being configured to arrest movement of the stylet upon engagement with a flat portion of any one of the plurality of teeth.

10. The targeting set of claim 9, the actuator including a slider positioned on an exterior of the housing, the slider being secured to the stylet such that the slider is configured to move the stylet relative to the housing, the housing including a plurality of depth indicators configured to indicate a depth of the stylet as the slider is moved relative to the housing.

11. The targeting set of claim 9, further comprising a depth stop, the depth stop being configured to selectively attach to at least a portion of the housing, the depth stop being further configured to receive a cannula associated with the stylet.

12. The targeting set of claim 11, the depth stop including one or more cannula stops, the one or more cannula stops being configured to selectively lock into a desired longitudinal position along a length defined by the cannula.

13. The targeting set of claim 9, the plurality of teeth being arranged relative to each other to permit distal advancement of the stylet relative to the housing, while preventing substantial proximal movement of the stylet relative to the housing.

* * * * *